US012252713B2

(12) United States Patent
Forman et al.

(10) Patent No.: US 12,252,713 B2
(45) Date of Patent: *Mar. 18, 2025

(54) CELL HYBRIDS AS VIRUS PACKAGING CELLS FOR HIGH EFFICIENCY PRODUCTION OF GENE THERAPY VECTORS AND VIRAL VACCINES

(71) Applicant: CHO Plus, Inc., South San Francisco, CA (US)

(72) Inventors: Lawrence Forman, San Mateo, CA (US); Kathy Ngo, San Francisco, CA (US)

(73) Assignee: Cho Plus, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/368,338

(22) Filed: Sep. 14, 2023

(65) Prior Publication Data

US 2024/0043810 A1 Feb. 8, 2024

Related U.S. Application Data

(60) Division of application No. 18/332,612, filed on Jun. 9, 2023, and a continuation of application No. PCT/US2023/024973, filed on Jun. 9, 2023.

(60) Provisional application No. 63/350,863, filed on Jun. 9, 2022.

(51) Int. Cl.
*C12N 5/071* (2010.01)
*C12N 15/86* (2006.01)

(52) U.S. Cl.
CPC ........... *C12N 5/0686* (2013.01); *C12N 15/86* (2013.01); *C12N 2511/00* (2013.01); *C12N 2750/14143* (2013.01); *C12N 2750/14152* (2013.01)

(58) Field of Classification Search
CPC .. C12N 5/0686; C12N 15/86; C12N 2511/00; C12N 2750/14143; C12N 2750/14152
See application file for complete search history.

(56) References Cited

U.S. PATENT DOCUMENTS

| | | |
|---|---|---|
| 6,989,264 B2 | 1/2006 | Atkinson et al. |
| 7,745,592 B2 | 6/2010 | Massie et al. |
| 8,703,480 B1 | 4/2014 | Liu et al. |
| 8,728,759 B2 | 5/2014 | Xu et al. |
| 8,828,719 B2 | 9/2014 | Cain et al. |
| 9,441,245 B2 | 9/2016 | Bovolenta et al. |
| 10,329,594 B1 * | 6/2019 | Forman ............ C12N 5/12 |
| 11,013,250 B2 | 5/2021 | Vrljic et al. |
| 11,441,132 B2 | 9/2022 | Barabas et al. |
| 11,649,449 B2 | 5/2023 | Forman |
| 2004/0077090 A1 | 4/2004 | Short |
| 2008/0145861 A1 | 6/2008 | Rapp et al. |
| 2012/0015841 A1 | 1/2012 | Shekdar et al. |
| 2019/0292562 A1 | 9/2019 | Mittal |

FOREIGN PATENT DOCUMENTS

| | | |
|---|---|---|
| EP | 2316955 B1 | 10/2017 |
| WO | 8705930 A1 | 10/1987 |
| WO | 0240665 A2 | 5/2002 |
| WO | 2006027202 A1 | 3/2006 |
| WO | 2018232265 A1 | 12/2018 |
| WO | 2020251537 A1 | 12/2020 |
| WO | 2023100107 A1 | 6/2023 |
| WO | 2023239928 A1 | 12/2023 |

OTHER PUBLICATIONS

Williamson CD, DeBiasi RL, Colberg-Poley AM. Viral product trafficking to mitochondria, mechanisms and roles in pathogenesis. Infect Disord Drug Targets. Feb. 2012; 12(1):18-37. (Year: 2012).*
Chakrabarti L, Mathew A, Li L, Han S, Klover J, Albanetti T, Hawley-Nelson P. Mitochondrial membrane potential identifies cells with high recombinant protein productivity. J Immunol Methods. Jan. 2019;464:31-39. (Year: 2019).*
Van Olphen AL, Mittal SK. Development and characterization of bovine x human hybrid cell lines that efficiently support the replication of both wild-type bovine and human adenoviruses and those with E1 deleted. J Virol. Jun. 2002;76(12):5882-92. (Year: 2002).*
Ghani K, Cottin S, Kamen A, Caruso M. Generation of a high-titer packaging cell line for the production of retroviral vectors in suspension and serum-free media. Gene Ther. Dec. 2007; 14(24):1705-11. (Year: 2007).*
Landgrebe D, Kasper C, Scheper T. Increasing productivity of hybridoma cell lines by sorting by side scattering light. BMC Proc. Nov. 22, 2011;5 Suppl 8(Suppl 8):P83. (Year: 2011).*
Bulcha JT, Wang Y, Ma H, Tai PWL, Gao G. Viral vector platforms within the gene therapy landscape. Signal Transduct Target Ther. Feb. 8, 2021;6(1):53. (Year: 2021).*

(Continued)

*Primary Examiner* — Nicole Kinsey White
*Assistant Examiner* — Ruixue Wang
(74) *Attorney, Agent, or Firm* — Michael Schiff

(57) ABSTRACT

This disclosure provides a technology for adapting host cells to maximize production and improve quality of viral vectors and particles. Cell hybrids are formed from parental cell lines, and divided or cloned into multiple aliquots for testing. Aliquots are chosen that have high production capacity and phenotypic features for virus production, such as an optimal level of intracellular organelles, and used to establish producer cell lines. The producer cells can be genetically altered to express a transgene that encodes viral elements for production of the viral vectors or particles with a therapeutic payload. The hybrid producer cells generate more viral vectors or particles per cell with higher functional titer, thereby lowering the cost of production of pharmaceutical agents for use in gene therapy and immunization.

20 Claims, 8 Drawing Sheets

(56) References Cited

OTHER PUBLICATIONS

Bulcha et al., "Viral Vector Platforms Within the Gene Therapy Landscape", Signal Transduction and Targeted Therapy, vol. 6, No. 53, Available Online At: https://www.nature.com/articles/s41392-021-00487-6, Feb. 8, 2021, pp. 1-24.
Chan et al., "Engineered AAVs for Efficient Noninvasive Gene Delivery to the Central and Peripheral Nervous Systems", Nature Neuroscience, vol. 20, No. 8, Aug. 2017, pp. 1172-1179.
Colberg-Poley et al., "Human Cytomegalovirus UL37 Immediate-Early Regulatory Proteins Traffic Through the Secretory Apparatus and to Mitochondria", Journal of General Virology, vol. 81, No. 7, Jul. 2000, pp. 1779-1789.
Cook et al., "Peroxisome Plasticity at the Virus-Host Interface", Trends in Microbiology, vol. 27, No. 11, Nov. 2019, pp. 906-914.
Das et al., "Tet-On Systems for Doxycycline-inducible Gene Expression", Current Gene Therapy, vol. 16, No. 3, Jun. 2016, pp. 156-167.
Dederer et al., "Cooperation of Mitochondrial and ER Factors in Quality Control of Tail-anchored Proteins", eLife, vol. 8, Jun. 7, 2019, 23 pages.
Fenyo et al., "Surface Antigens and Release of Virus in Hybrid Cells Produced by the Fusion of A9 Fibroblasts with Moloney Lymphoma Cells", Experimental Cell Research, vol. 68, No. 2, 1971, pp. 323-331.
Gray et al., "Optimizing Promoters for Recombinant Adeno-Associated Virus-Mediated Gene Expression in the Peripheral and Central Nervous System Using Self-Complementary Vectors", Human Gene Therapy, vol. 22, No. 9, Sep. 2011, pp. 1143-1153.
James et al., "Crystal Structure of the SF3 Helicase from Adeno-Associated Virus Type 2", Structure, vol. 11, No. 8, Aug. 2003, pp. 1025-1035.
James et al., "Structure of Adeno-Associated Virus Type 2 Rep40-ADP Complex: Insight into Nucleotide Recognition and Catalysis by Superfamily 3 Helicases", Proceedings of the National Academy of Sciences of the United States of America, vol. 101, No. 34, Aug. 24, 2004, pp. 12455-12460.
Janknecht, "A Growing Coactivator Network", Nature, vol. 383, Sep. 5, 1996, pp. 22-23.
Kafri et al., "A Packaging Cell Line for Lentivirus Vectors", Journal of Virology, vol. 73, No. 1, Jan. 1999, pp. 576-584.
Knowles et al., "Susceptibility of Primate-Mouse Hybrid Cells to SV40", Journal of Cellular Physiology, vol. 78, Available Online At: https://onlinelibrary.wiley.com/doi/10.1002/jcp.1040780102, Aug. 1971, pp. 1-8.
Koch et al., "ER-SURF: Riding the Endoplasmic Reticulum Surface to Mitochondria", International Journal of Molecular Sciences, vol. 22, No. 17, Sep. 6, 2021, 13 pages.
Kouzarides, "Chromatin Modifications and their Function", Cell, vol. 128, No. 4, Feb. 23, 2007, pp. 693-705.
Li et al., "Histone Deacetylase 1 and p300 Can Directly Associate with Chromatin and Compete for Binding in a Mutually Exclusive Manner", PLoS One, Journal of Virology, vol. 9, No. 4, Apr. 10, 2014, 12 pages.
Linden et al., "Molecular Biology of Adeno-Associated Viruses", Contrib Microbiol Immunol, vol. 4, 2000, pp. 68-84.
Lochmann et al., "NC-Mediated Nucleolar Localization of Retroviral Gag Proteins", Virus Research, vol. 171, No. 2, Feb. 2013, pp. 304-318.
Matsushita et al., "The Adenovirus E1A and E1B19K Genes Provide a Helper Function for Transfection-based Adeno-associated Virus Vector Production", Journal of General Virology, vol. 85, Aug. 2004, pp. 2209-2214.
Mavinakere et al., "Internal Cleavage of the Human Cytomegalovirus UL37 Immediate-early Glycoprotein and Divergent Trafficking of Its Proteolytic Fragments", Journal of General Virology, vol. 85, No. 7, Jul. 1, 2004, pp. 1989-1994.
Mougiakos et al., "CRISPR Transposons on the Move", Cell Host & Microbe, vol. 29, No. 5, May 12, 2021, pp. 675-677.
Application No. PCT/US2023/024973, International Search Report and Written Opinion, Mailed On Sep. 22, 2023, 13 pages.
Qiao et al., "A Novel Gene Expression Control System and Its Use in Stable, High-Titer 293 Cell-Based Adeno-Associated Virus Packaging Cell Lines", Journal of Virology, vol. 76, No. 24, Dec. 2002, pp. 13015-13027.
Qiao et al., "Feasibility of Generating Adeno-Associated Virus Packaging Cell Lines Containing Inducible Adenovirus Helper Genes", Journal of Virology, vol. 76, No. 4, Feb. 2002, pp. 1904-1913.
Ravindran et al., "Opportunistic Intruders: How Viruses Orchestrate ER Functions to Infect Cells", Nature Reviews Microbiology, vol. 14, Jul. 2016, pp. 407-420.
Sanber et al., "Construction of Stable Packaging Cell Lines for Clinical Lentiviral Vector Production", Scientific Reports, vol. 5, No. Article No. 9021, Mar. 12, 2015, 10 pages.
Sharmin et al., "Insulin-like Growth Factor-1 Induces IRE1-XBP1-Dependent Endoplasmic Reticulum Biogenesis in Bovine Mammary Epithelial Cells", Journal of Dairy Science, vol. 104, No. 11, Nov. 2021, pp. 12094-12104.
Smith et al., "Peroxisomes Take Shape", Nature Reviews Molecular Cell Biology, vol. 14, No. 12, Dec. 2013, pp. 803-817.
Strang et al., "Host Cell Nucleolin is Required to Maintain the Architecture of Human Cytomegalovirus Replication Compartments", mBio, vol. 3, No. 1, Jan./Feb. 2012, 11 pages.
Tanenbaum et al., "A Protein-Tagging System for Signal Amplification in Gene Expression and Fluorescence Imaging", Cell, vol. 159, No. 3, Oct. 9, 2014, pp. 635-646.
Topf et al., "Quantitative Proteomics Identifies Redox Switches for Global Translation Modulation by Mitochondrially Produced Reactive Oxygen Species", Nature Communications, vol. 9, No. 1, Jan. 22, 2018, 17 pages.
Van Olphen et al., "Development and Characterization of Bovine x Human Hybrid Cell Lines That Efficiently Support the Replication of both Wild-Type Bovine and Human Adenoviruses and Those with E1 Deleted", Journal of Virology, vol. 76, No. 12, 2002, pp. 5882-5892.
Williamson et al., "Viral Product Trafficking to Mitochondria, Mechanisms and Roles in Pathogenesis", Infectious Disorders—Drug Targets, vol. 12, No. 1, Feb. 2012, pp. 18-37.
Wistuba et al., "Subcellular Compartmentalization of Adeno-Associated Virus Type 2 Assembly", Journal of Virology, vol. 71, No. 2, Feb. 1997, pp. 1341-1352.
Yuan et al., "A Versatile Adeno-Associated Virus Vector Producer Cell Line Method for Scalable Vector Production of Different Serotypes", Human Gene Therapy, vol. 22, No. 5, Available Online at: https://www.ncbi.nlm.nih.gov/pmc/articles/PMC3081441/pdf/hum.2010.241.pdf, May 2011, pp. 613-624.
Corresponding International Application No. PCT/US2023/024973, International Preliminary Report on Patentability (IPRP) mailed on May 10, 2024, 5 pages.
U.S. Appl. No. 18/332,612, Non-Final Office Action mailed on Mar. 14, 2024, 38 pages.
Ghani et al., "Generation of a High-titer Packaging Cell Line for the Production of Retroviral Vectors in Suspension and Serum-free Media", Gene Therapy, vol. 14, Oct. 11, 2007, pp. 1705-1711.
Banskota et al., "Engineered Virus-like Particles for Efficient in Vivo Delivery of Therapeutic Proteins", Cell, vol. 185, No. 2, Jan. 20, 2022, 33 pages.
Dumont et al., "Human Cell Lines for Biopharmaceutical Manufacturing: History, Status, and Future Perspectives", Critical Reviews in Biotechnology, vol. 36, No. 6, Dec. 2016, pp. 1110-1122.
Ibanez et al., "Experimental Dissection of the Lytic Replication Cycles of Herpes Simplex Viruses in Vitro", Frontiers in Microbiology, vol. 9, Article 2406, Oct. 11, 2018, pp. 1-23.
Javadov et al., "Mitochondria in Health and Diseases", Cells., vol. 9, No. 5, May 9, 2020, pp. 1-9.
Kaczmarczyk et al., "Protein Delivery Using Engineered Virus-like Particles", Proceedings of the National Academy of Sciences of the United States of America, vol. 108, No. 41, Oct. 11, 2011, pp. 16998-17003.
Le et al., "Core Labeling of Adenovirus With EGFP", Virology, vol. 351, No. 2, Aug. 1, 2006, pp. 291-302.

(56) References Cited

OTHER PUBLICATIONS

Mahen et al., "Cell-cell Fusion of Genome Edited Cell Lines for Perturbation of Cellular Structure and Function", Journal of Visualized Experiments, vol. 154, Dec. 7, 2019, pp. 1-7.
Application No. PCT/US2023/024973, International Preliminary Report on Patentability, Mailed On May 10, 2024, 5 pages.
Application No. PCT/US2023/083811, International Search Report and Written Opinion, Mailed On Jul. 4, 2024, 12 pages.
Tark et al., "Generation of a Persistently Infected MDBK Cell Line With Natural Bovine Spongiform Encephalopathy (BSE)", Public Library of Science One, vol. 10, No. 2, Feb. 3, 2015, pp. 1-11.

* cited by examiner

FIG. 5
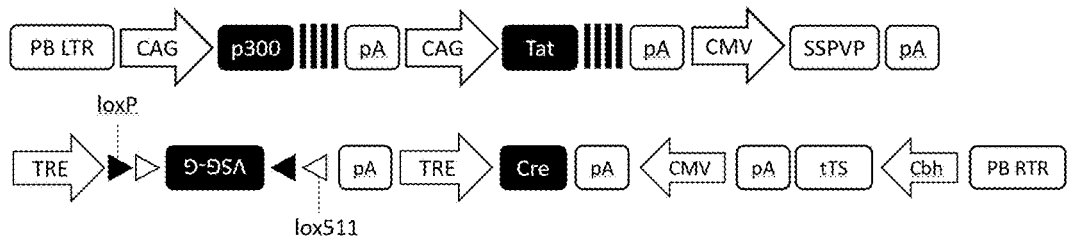
FIG. 6A, 6B, and 6C
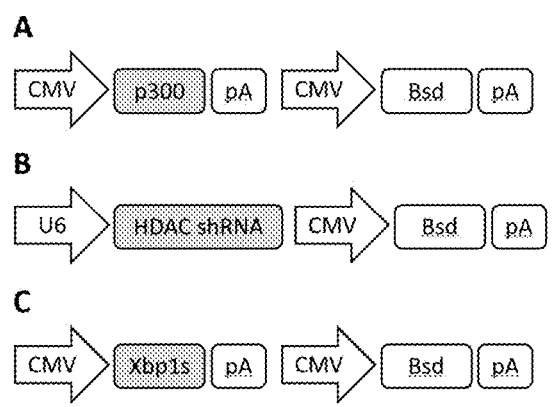
FIG. 7
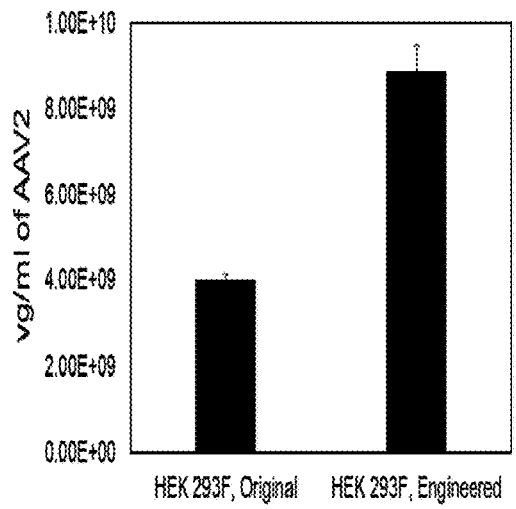

FIG. 8

10⁸ Fused Cells - Mixed Pool

Label and sort 1 x 10⁶ of desired population of
high mitochondria and high reactive oxygen species (ROS)

Expand to 10⁸ cells

Label and sort 1 x 10⁶ of desired population of
high mitochondria and high ROS

Expand to 10⁸ cells

Label and sort 1 x 10⁶ of desired population of
high mitochondria and high ROS

Single cell cloning of individual host cells on 96-
well plates

Expand clones and
take samples for screening

CELL HYBRIDS AS VIRUS PACKAGING CELLS FOR HIGH EFFICIENCY PRODUCTION OF GENE THERAPY VECTORS AND VIRAL VACCINES

RELATED APPLICATION

This patent application is a divisional of U.S. patent application Ser. No. 18/332,612, filed Jun. 9, 2023 (pending), which claims the priority benefit of U.S. provisional patent application 63/350,863, filed Jun. 9, 2022. This patent application is also a continuation of international application PCT/US2023/024973, filed Jun. 9, 2023 (pending), which claims the priority benefit of the same U.S. provisional patent application 63/350,863, filed Jun. 9, 2022. Each of these previously filed patent applications is hereby incorporated herein by reference in its entirety for all purposes.

TECHNICAL FIELD

This disclosure relates generally to the production of pharmaceutical compounds that contain viral components. It also relates to the modification, selection, and genetic alteration of host cells for high levels of production of pharmaceutical products with improved biological and pharmacological characteristics.

BACKGROUND

The past decade has seen viral vector based therapies become a bona fide option in clinical medicine. A dozen therapies using viral vectors have been approved by the FDA, spanning three different types of viral vectors: adeno-associated virus (AAV), lentivirus, and herpes simplex virus. Adenovirus vectors have been approved as immunogenic compositions for treatment of infections diseases such as COVID 19. With about 25 viral vector therapeutics currently in late-stage development and another 120 in Phase II trials, the number of viral vectors approved for commercial production will increase rapidly (E. Capra et al., McKinsey and Company, 2022).

The first gene therapy vectors were typically developed for treatment of rare diseases. The emerging interest in treating more common conditions requires higher yields and a lower cost of goods. Over the last few years, large contract development and manufacturing organizations (CDMOs) have invested billions of dollars in production facilities for viral vectors. This burgeoning interest is promising, but the rapid influx of money and development of new technology have not solved the bottlenecks and challenges of viral vector manufacturing.

Currently, lack of standardization and low yields are part of the challenge. Physical characteristics and functional requirements vary considerably between different vectors. A high degree of process optimization is still needed for each product. Low recovery from chromatography steps means that yields are typically below 50 percent (M. May, Biotech. Eng. News, Aug. 2, 2021). By way of comparison, the manufacture of therapeutic antibodies like Humira® and Rituxan® and biosimilars is done using standardized platforms, and typically achieves yields higher than 90 percent.

The owners of the technology described in this disclosure previously developed a system for increasing production of monoclonal antibodies in producer cell lines by over four-fold. U.S. Pat. No. 10,329,594. Cultured cells such as CHO cells are fused together, and hybrids are selected for a high content of endoplasmic reticulum or Golgi apparatus. Unfortunately, the intracellular machinery that is needed for making viral vectors is quite different. Replication of most viruses occurs in the cytoplasm, not the ER, and must be coordinated within the cell to achieve proper vector assembly.

SUMMARY OF THE INVENTION

This disclosure provides a technology for adapting host cells to maximize production and improve quality of viral vectors and particles. Cell hybrids are formed from parental cell lines, and divided or cloned into multiple aliquots for testing. Aliquots are chosen that have high production capacity and phenotypic features for virus production, such as an optimal level of intracellular organelles, and used to establish producer cell lines. The producer cells can be genetically altered to express a transgene that encodes viral elements for production of the viral vectors or particles with a therapeutic payload. The hybrid producer cells generate more viral vectors or particles per cell with higher functional titer, thereby lowering the cost of production of pharmaceutical agents for use in gene therapy and immunization.

In general terms, the technology put forth in this disclosure can be used for producing viral vectors or particles. The system is implemented by providing a starter population of cultured cells; forming cell hybrids from the starter population, each comprising two or more cells, and genetically altering cell hybrids to express elements of a virus and a drug payload. The cells are then cultured to produce the viral vectors or particles containing said elements and encapsulating said drug payload.

Throughout this disclosure, the terms "fused cells", "cell hybrids", and "engineered cells" refer interchangeably to a cell made by combining two or more parental cells together to create a single cell bearing organelles and chromosomes from all parents within a combined plasma membrane. A "payload" is a polypeptide, polynucleotide, or any other compound or composition that is encapsulated in a viral capsid or other macromolecular package. Exemplary payloads are a reporter gene for cell screening, or a therapeutic payload for use in medical treatment. A "viral vector" is a capsid configured to cause expression of a nucleotide it contains when administered in vivo. A "viral particle" is a capsid configured to deliver a protein or other payload into cells when administered in vivo. Cells that are "genetically altered" contain an expressible transgene, either within the genome of the cell or as a plasmid that is expressed elsewhere in the cell.

A way of implementing the technology of this disclosure is to create a bank of producer cell lines that can be sourced for manufacturing capsids containing different payloads. Producer cell lines for high efficiency production of viral vectors or particle are made by providing a starter population of cultured cells, forming cell hybrids from the starter population, each comprising the contents of two or more parental cells. The hybrids are distributed into a plurality of aliquots, which are then sampled for testing The samples are genetically altered to express one or more transgenes that encodes elements of a viral system, plus a reporter means for determining how efficiently the genetically altered cells from each aliquot are producing viral components or capsids. The reporter means may be the viral components themselves or a drug payload. For screening purposes, it is convenient to use a reporter gene that encodes an easily expressible gene product, such as a protein that generates an optical signal like a green fluorescent protein or luciferin.

For screening purposes, it is often convenient to use a means of transient transfection, although stable transfection may also be used. The multiple transgenes can be transfected not the cells together or separately. Since different viruses and different viral serotypes may be optimally expressed in cells with different phenotypes, it is often beneficial (though not required) to use the same virus or serotype for screening that will ultimately be used to express a viral vector or particle for therapeutic use.

After transfection, the user characterizes each of the samples by mearing production and/or quality viral vectors or particles containing a product of the reporter gene by each of the samples. Aliquots containing cells having desirable attributes are expanded in culture to establish producer cell lines. Optionally, the user may conduct one or more additional cycles of aliquoting, characterizing, and expanding to further enrich for cells having desirable phenotypes and/or virus production capacity. If desired, the cells can be cloned at any time in the process: either as a means of aliquoting the cells at the outset, or at subsequent steps to stabilize cell characteristics.

Alternatively or in addition, aliquots of cells can be separated or chosen according to cell characteristics that have empirically been determined to accompany favorable virus production. This can be done, for example, as part of the aliquoting process, where cells are sorted or segregated according to high or low intracellular content of one or more organelles such as mitochondria, peroxisomes, endoplasmic reticulum, Golgi apparatus, or nucleoli, and/or one or more cytoplasmic or transcellular features such as reactive oxygen species (ROS), cellular redox, or pH, in any combination. Phenotype based segregation or selection can occur sequentially or simultaneously with assessment of viral production, whereby the ultimate selection of cells may be a combination of phenotype and production capacity.

Identifying and choosing which aliquots or clones to expand can be based on which aliquots contain cell hybrids produce more viral capsids per cell., or which aliquots produce a greater proportion of capsids that are filled with the reporter gene, or a combination of the two. Depending on the user's objectives, the technology of this disclosure can be implemented by using as the starter cell population a single cell line, such as CHO cells, mouse myeloma NSO cells, mouse myeloma SP2/0 cells, human embryonic kidney 293 (HEK 293) cells, baby hamster kidney 21 (BHK-21) cells, VERO cells, PER.C6 cells, and HeLa cells; using autotypic hybrids thereof; or using combinations or hybrids of such cells with cells from another cell line or with primary cells.

For industrial-scale production of viral vectors and particles for use in therapy or for other purposes, cells from the established cell bank are genetically altered to express a transgene encoding one or more elements of a virus, plus a transgene that constitutes or encodes the desired payload. The transfection can be transient, or stable (permanent). The transgenes for the virus and the payload can be inserted into the genome of the producer cells transiently or stably in various combinations. For example, a producer cell line can be stably transfected with components needed for virus assembly to establish a producer cell line dedicated for a chosen type of virus. The dedicated producer line can subsequently be transiently transfected to contain different payloads depending on the clinical objective.

This disclosure includes producer cell lines adapted for high efficiency or high quality production of viral vectors or particles, established according to any of the aforesaid methods and processes. Optionally, the producer cell lines may be genetically altered with a plasmid encoding one or more elements of a virus (such as the Rep and Cap genes of AAV), and optionally with a helper plasmid (for example, encoding adenovirus genes that promote AAV packaging), thereby adapting the cells to produce a viral vector or particle containing said elements. Some producer cells of this technology can be characterized as a hybrid of two or more parental cells from a starter cell population, wherein the producer cells comprise an expressible transgene that encodes one or more elements of a virus, whereby the cells are configured to produce a viral vector or particle containing said elements.

Such producer cells may further comprise a transgene constituting or encoding a payload, thereby adapting the cells to produce a viral vector or particle encapsulating said payload. Examples of such payloads comprise any one or more of the following: (1) a nucleic acid configured for expression in a human subject in vivo upon administration to the subject; (2) a protein configured for delivery into cells of the subject upon administration of the particle to the subject; (3) a nucleic acid or a protein configured for transfection into cells ex vivo; and/or (4) a reporter gene as set forth above.

Any of the producer cells disclosed herein may produce specified numbers of viral vectors or particles per cell, as set forth below. Alternatively or in addition, the producer cells disclosed herein (compared with cells from the starter cell population that have been genetically altered with the same transgenes) may be characterized as producing more viral vectors or particles; producing viral vectors or particles with higher functional titer; and/or producing viral vectors or particles with a higher proportion filled with a particular payload, as set forth below.

This disclosure provides methods of manufacture of viral vector or particles encapsulating a payload, for example by culturing cells from an established producer cell line of this disclosure. The viral vectors or particles produced thereby may be formulated as a medicament under GMP conditions to produce a pharmaceutical product that is suitable for human administration. The viral vectors or particles produced thereby may also be configured for ex vivo therapy of a human subject in need thereof.

This disclosure provides methods of therapy by administering to a subject a viral vector or particle put forth above. Alternatively, the vectors and particles may be used for ex vivo therapy by contacting them with a plurality of cells (usually autologous or allogenic to a subject), and thereafter administering the cells to the subject.

Exemplary viral systems that can be used in any aspect of this disclosure are adeno-associated virus (AAV) vectors or particles and select serotypes thereof. In principle, the technology of this disclosure can be used to establish producer cell lines for any viral system, such as adenoviruses, alphaviruses, flaviviruses, herpes simplex viruses (HSV), measles viruses, rhabdoviruses, retroviruses, lentiviruses, Newcastle disease virus (NDV), poxviruses, and picornaviruses.

Viral vectors manufactured in accordance with this disclosure can be used for treatment of a variety of human diseases or conditions. The payload may be a polynucleotide encoding a gene product for genetic therapy of a human subject in need thereof. The payload may be a target antigen of a pathogenic microbe such as SARS-CoV-2, or a nucleic acid encoding said target antigen, for eliciting an immune response in a subject in need thereof against said microbe.

Various aspects, embodiments, features, and characteristics of the invention are described in the sections that follow, the accompanying drawings, and the appended claims.

BRIEF DESCRIPTION OF THE DRAWINGS

FIG. 5 is a gene map of an inducible STAC cassette for amplified synergistic activation of VSV-G gene as well as packaging genes.

FIG. 6A is a diagram of a p300 integration gene cassette. p300 gene is flanked by CMV promoter and SV40 poly A tail. FIG. 6B shows a HDAC shRNA gene cassette. HDAC shRNA is flanked by U6 promoter for shRNA expression. FIG. 6C shows a spliced Xbp1 (Xbp1s) gene cassette.

FIG. 7 shows a workflow used to screen fused HEK 293 cells according to intracellular content of mitochondria and reactive oxygen species (ROS).

FIG. 8 is a set of gene maps for the plasmids used to make AAV vectors containing an enhanced green fluorescent protein (EGFP) reporter gene for purposes of screening cell hybrids for virus production.

DETAILED DESCRIPTION

This disclosure provides improved cell lines for manufacture of pharmaceutical agents containing viral elements, considerably reducing the cost of commercial production. The cell lines are obtained by selecting cells from a mixed population for one or more characteristics that support virus or virus production on a non-specific basis, such as the level of mitochondria, endoplasmic reticulum, Golgi apparatus, and/or other desired phenotypic features, compared with other cells in the starter mixture. Particularly effective producer cell lines can be obtained by preparing the cells for functional selection by making cell hybrids. Expressible genes containing elements of the intended viral vector or particle may be transfected into the cells before or after one or more cycles of fusion and selection.

1. Overview

Figure 1:
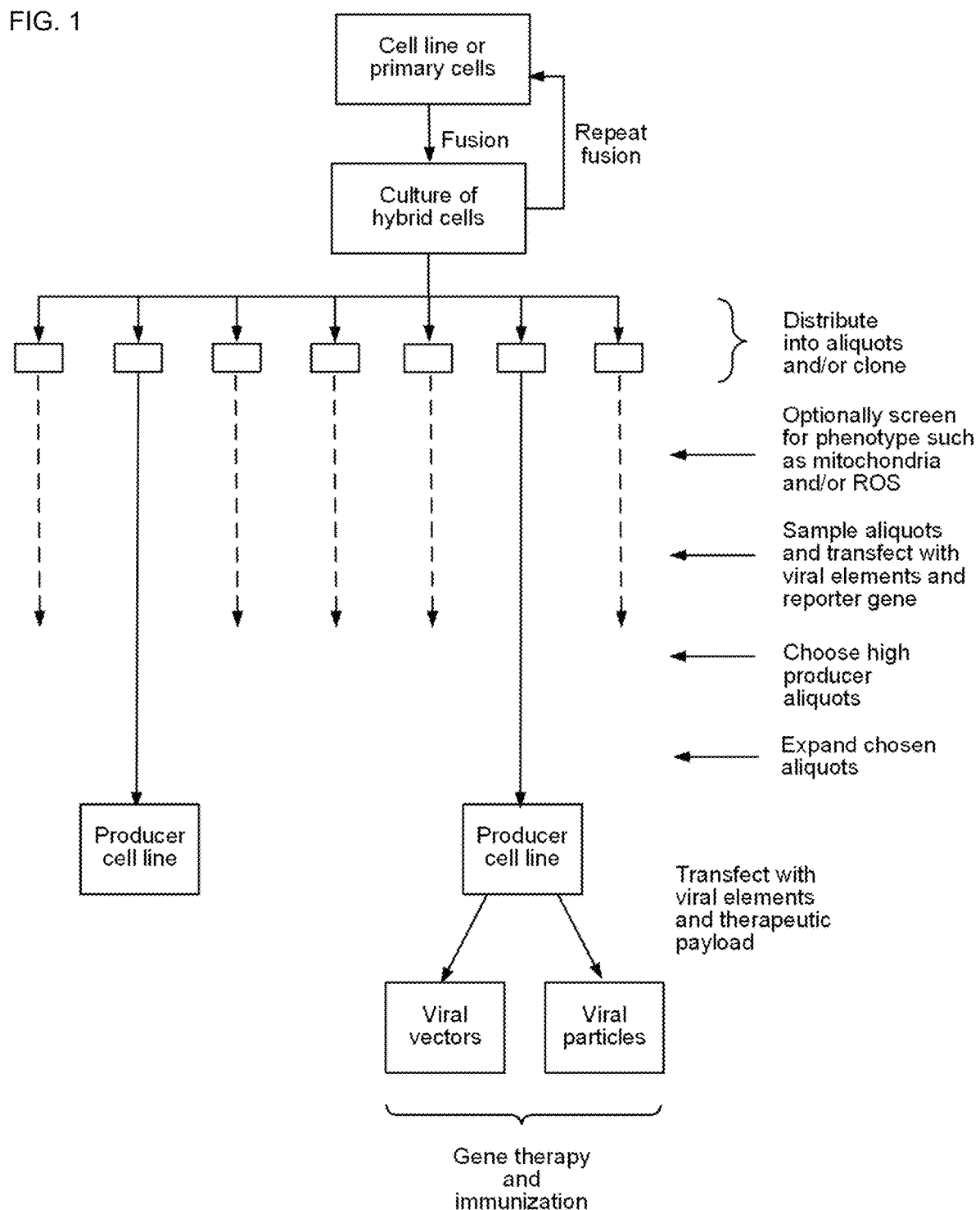
FIG. 1 is a workflow for obtaining hybrid cell lines with high virus production capacity. Cells are fused together to produce an engineered cell population. The population is then cloned or separated into separate aliquots, optionally taking into account desirable cell phenotypes (such as intracellular organelle content). The separate clones or aliquots are transiently transfected to express viral elements and a reporter protein, and high producer cells are identified. The chosen cells are expanded to establish a bank of producer cell lines. The producer cells can be transfected to express a viral vector or particle encapsulating a therapeutic payload for gene therapy or immunization.

FIG. 1 is a general scheme that outlines a suitable workflow by which the technology of this disclosure can be implemented.

Cells from a chosen source (for example, an established cell line) are fused together in multiple cycles to generate a population of hybrids that are heterogeneous in their ability to synthesize viral vectors or particles. To obtain cells from the population that are high producers, the population is partitioned into a plurality of separate aliquots or clones. As part of the partitioning, the cells may be screened or separated according to particular phenotypic features that are known or suspected of being beneficial to high levels of viral capsid production or filling. A sample from each of the separate aliquots or clones are individually tested for their ability to produce high quantities or high titers of vectors or particles. Aliquots of cells that are now proven to be high producers are expanded, and used to establish one or more producer cell lines.

The banked producer cells can then be sourced for industrial-scale production of one or a variety of therapeutic viral vectors or particles, especially using viral components of the same species and serotype that were used for screening. The cells selected for industrial production can be transfected in the same manner used for screening, with the exception that the reporter gene is substituted with a therapeutic payload. The final transfection can be transient, or the viral elements can be integrated into the genome of the producer cell with an inducible promoter—whereafter different payloads can be encapsulated into the same viral system by transient transfection.

Other workflows can be effective, depending on the choice of a viral system and the user's objectives. The various aspects of the technology of this disclosure can be practiced in any combination and any order which is effective to generate the user's intended viral vectors or particles.

2. Benefits of this Technology

Depending on the mode of practice and application, aspects of this disclosure described in this disclosure can be used to select cell hybrids that produce viral vectors and particles at a higher functional titer per volume of culture fluid. This in turn has the following benefits.

reduces the cost of production of viral vectors and particles for clinical use, thereby improving access to such therapeutic agents;

reduces the need to enlarge or build new GMP production facilities as market size increases;

provides for GMP production of kilogram quantities of finished protein product with relatively small or fewer bioreactors, creates established producer cell lines suitable for high-level expression of a family of different vectors and vaccines, as needed;

decreases cloning or selection steps that are needed following integration of the gene to be expressed;

improves product quality; and provides high quality low volume research materials, thereby reducing the time needed to initiate and complete clinical trials.

The technology of this disclosure can also be used to improve the loading of viral capsids produced, thereby increasing the effective titer of the preparation. Before this discovery, AAV capsids produced by host cells are largely empty (10-30 percent full is the industry average), which adversely affects the efficacy and safety of AAV drug products, increasing the risk of immunogenicity. Provided below is a technology for selecting cells with higher content of mitochondria and reactive oxygen species, which results in a two-fold increase in the proportion of capsids bearing a payload.

3. Rationale

The technology of this disclosure for packaging vectors such as lentivirus, adenovirus, and adeno associated virus (AAV) take advantage of the dependency of cellular compartments of key proteins involved in the packaging and replication of viruses.

The physical association between the endoplasmic reticulum (ER), mitochondria, peroxisomes, and nucleoli have been implicated in production of viral proteins. The MAM, transient contact sites between the ER and mitochondria provides calcium microdomains for cellular signaling such as activation of $Ca^{++}$-dependent metabolic enzymes. Evidence of ER-to-mitochondria trafficking have been associated with the human cytomegalovirus UL37 proteins, wherein a highly conserved sequence drives the translocation of these proteins into the ER.

Viral mitochondrial-localized inhibitor of apoptosis (vMIA) functions in both ER and mitochondria. Besides viral proteins, viral RNAs have also been able to target mitochondria (Reeves et al., 2007). Other key viruses in which ER and/or mitochondria trafficking is critical includes the hepatitis C viruses (HCV) and related viruses in the family of Flaviviridae, polyomaviruses, rotaviruses, coronaviruses, polioviruses, enteroviruses, Hepatitis E virus, HIV-1, adeno-associated viruses (AAV; reviewed in Williamson et al., 2012; Ravindran et al., 2016). The adenovirus E1B19K packaging protein is required for virus packaging of AAV and is localized in the mitochondria.

Peroxisomes and nucleoli are important organelles for virus production. Peroxisomes serves as hubs for reaction oxygen species (ROS), can form de novo from the ER and are hijacked by various types of viruses wherein viral proteins are sequestered in these organelles. These include HCV, HCMV, and Kaposi's sarcoma-associated herpes virus (KSHV). The cell nucleus plays an incredibly integral role in virus production. For the majority of viruses, cytoplasmic to nuclear trafficking, and likewise retrograde nuclear to cytoplasmic signaling are both critical for virus production. There are numerous examples of nuclear transport of viral proteins.

Viral proteins have observed to be localized to the nucleoli and the functional importance of nucleoli in virus replication have only been recently dissected. The importance of nucleoli in virus replication is most well studied in HCMV. In another example, capsid proteins of AAV2 have been shown to sequester in the nucleoli during virus packaging. In yet another instance, the Gag protein of the Rous Sarcoma Virus (RSV) is retained in the nucleoli and this retention to critical for efficient packaging.

The technology of this disclosure leverages the subcellular organelles (exemplified by endoplasmic reticulum, mitochondria, peroxisomes, and nucleoli) to further enhance the manufacturing of viruses to create a super manufacturing cell line. These benefits are realized through the engineering cell lines selecting for attributes of high ER (which includes enhanced unfolded protein response), mitochondria content, peroxisomes, or nucleoli in singularity or plurality as discussed in this disclosure. Virus production can be increased by selecting cells from a mixed cell population for higher levels subcellular machinery or biochemistry that support increased virus production, compared with other hybrids or parental cells in the starting mixture.

At least one of the phenotypic features is selected that is not necessarily specific for production of a particular virus. The feature is not simply the level of expression of a protein of interest or a surrogate. Rather, it is a feature that supports production of a wide range of different viruses. Such features include the relative density of subcellular organelles, particularly those involved in the packaging of viruses and the relative level or concentration of enzymes that help package a variety of different proteins, e.g. HIV, adenoviruses and adeno-associated viruses (AAV).

Further enhancement of virus production can be achieved through stable gene copy amplification of viral genes critical for packaging and replication, histone modifiers, enhancers of protein biogenesis pathways, and transcriptional amplifiers to create a unique manufacturing cell line potentially capable of amplifying virus production by tens to hundreds of folds as described in this disclosure as compared to traditional host cell lines used in the industry for virus production.

4. Technological Approach

Repeated homotypic fusions of virus producer cells such as HEK 293 cells are believed to result in genome shuffling and amplification of whole chromosomes within individual cells. Cells are chosen that have desirable phenotypes lead to enhanced manufacturing capabilities. Fused cell hybrids are superior for production of viral vector, generating higher titer, higher capsid percent-full, and/or higher infectivity.

Figure 9A:
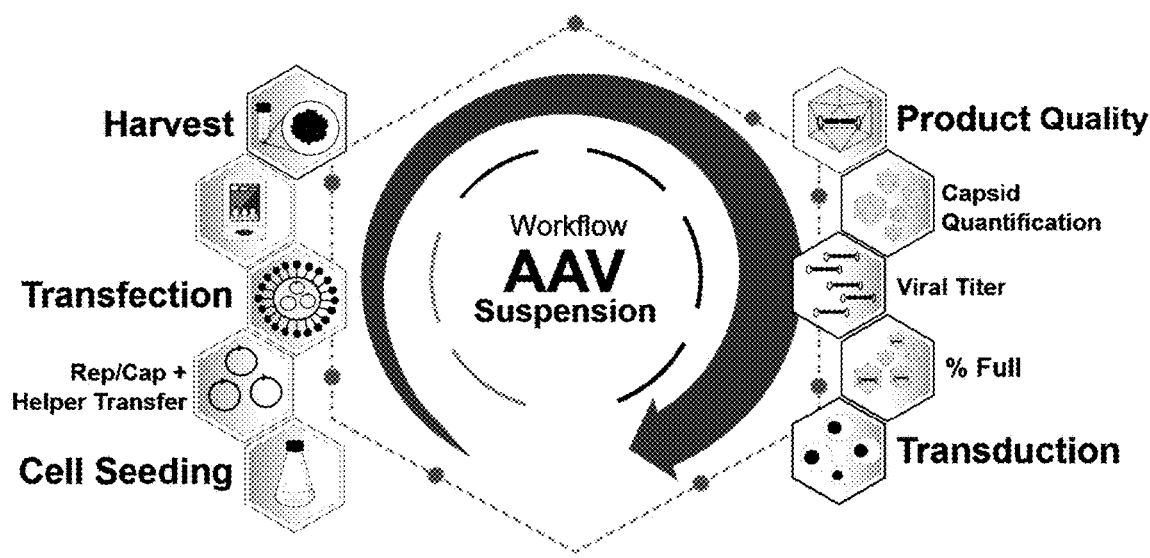
FIG. 9A shows a workflow used to produce AAV vectors using suspension HEK 293 cells as host. Left: cell seeding, transfection and harvesting of AAV particles from lysed cells. Right: assessment of product quality: capsid quantification, viral titer (or capsid concentration), percent full capsids, and functional titer by transduction.

FIG. 9A illustrates a suitable workflow for production of AAV vectors using suspension HEK 293 cells as host. Left: cell seeding, transfection and harvesting of AAV particles from lysed cells. Right: assessment of product quality: capsid quantification, viral titer (or capsid concentration), proportion of full capsids, and functional titer by transduction.

5. Demonstration of High Level Production of Viruses from Fused Cells

Cell fusion of HEK 293 cells was performed multiple times using PEG as a fusogenic agent to form autotypic hybrids (a plurality of cells from one cell line).

For packaging and production of adeno-associated viruses, serotype 2 (AAV2), un-engineered and engineered HEK 293F were transfected with a helper plasmid, a virus plasmin containing AAV Rep and Cap proteins, and a transfer plasmid expressing NeonGreen fluorescent protein under the control of a constitutive cytomegalovirus (CMV) early promoter, flanked by AAV2 inverted terminal repeats (ITRs), and an additional plasmid expressing microRNA, mi342 under the control of a ubiquitous CMV promoter. Transfections were performed using linear polyethyleneimine (PEI). Post-transfection, crude virus was extracted from cell lysates and virus was recovered by centrifugation. Quantitative PCR was used to measure viral copy number produced by un-engineered and engineered HEK 293 cell lines.

Figure 9B:
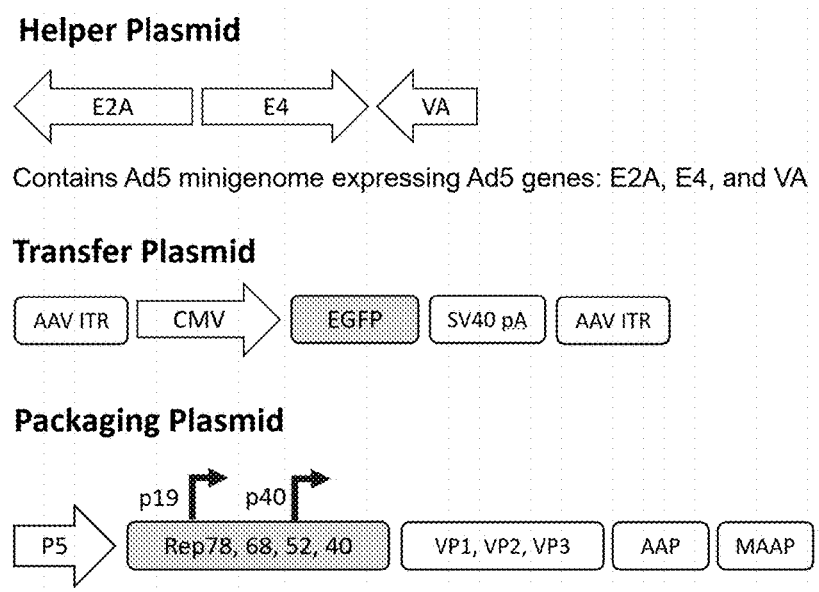
FIG. 9B shows the number of AAV2 viral particles that can be produced from fused HEK 293 cells.

FIG. 9B shows the number of viral particles that can be produced from fused cells. Viral genome of packaged AAV2 was measured by quantitative PCR following DNase I treatment. Primers targeting NeonGreen gene was used for the quantification and vg/ml of samples were determined using a commercial AAV2 reference virus with known vg/ml from Vigene Biosciences. Compared to un-engineered HEK 293F cell line, the engineered HEK 293F shows a 2.5-fold increase of viral genome produced.

6. Detailed Protocol

By way of illustration (and without implying any limitation on the claimed invention and equivalents thereof), producer cell lines for AAV vectors have been obtained according to the following protocol:

Step 1: Production of hybrids. A starting cell population of HEK 293 cells was used to make cell hybrids by using polyethylene glycol as fusogenic agent combined with gentle centrifugation to promote cell contact. Hybrids were cloned. Each clone was separated into aliquots, and sampled for transfection testing.

Step 2: Transfection. Sampled hybrid cell clones in suspension were transfected with chemical-based methods using a lipid polymer that complexes with negatively charged DNA to form lipopolyplexes via electrostatic interactions. Three plasmid vectors were used for transfection: 1) transfer vector expressing a fluorescent protein under the control of ubiquitous CMV promoter cassette flanked by AAV inverted terminal repeats; 2) helper vector cassette expressing adenovirus E4 gene for AAV DNA replication, adenovirus E2a gene and adenovirus VA RNA (virus-associated RNA) genes to enhance AAV mRNA stability and promote AAV capsid transcripts; and 3) packaging vector expressing Rep and Cap proteins specific serotype being assayed (AAV1, AAV2, and AAV5). Cells were harvested 72 hours post-transfection, lysed and assayed for AAV production.

Step 3: Determining production capability of cloned hybrids. AAV genomic copy number was measured by real-time quantitative PCR. Cell lysates were treated with DNase I to remove non-viral host genomic DNA. Real-time quantitative PCR by fluorescent detection was performed to determine viral genomic copy number. DNA primers bind to coding regions of fluorescent reporter within the transfected transfer vector in the assembled AAV and copy number was detected using fluorescence (methods used by previous figures.

Step 4: Determining AAV serotype-specific capsids. Biolayer interferometry (BLI) is an optical biosensing technology that analyzes biomolecular interactions in real-time without the need for fluorescent labeling. Interference patterns of white light or phase shift caused by analyte sample binding to immobilized ligand on biosensor probe was used to quantify the amount of AAV virus in an unknown sample. A small biosensor that binds specifically to AAV capsid protein for multiple serotypes (AAV1, AAV2, AAV5). For each serotype (AAV1, AAV2, and AAV5), a standard curve of a commercial AAV reference standard, with known concentration measured by other validated methods are used to back-calculate the concentration of AAV serotypes in unknown sample.

Step 5: Measuring the ratio of full to empty capsids. Ratio of full to empty capsids can be measured in unknown samples by biolayer interferometry. First, concentrations of AAV serotypes of unknown samples are measured as described above. For each serotype being measured, AAV capsids at a normalized concentration are first captured and immobilized on the biosensor. Following immobilization, AAV particles are lysed to release the packaged ssDNA and ssDNA is captured and measured using a biosensor probe that is conjugated to SSB protein wherein SSB protein binds specifically to ssDNA. For each serotype (AAV1, AAV2, and AAV5), a standard curve of a commercial AAV reference standard, with known full-to-empty capsids ratio measured by other validated methods are used to back-calculate the ratio of AAV serotypes in unknown sample.

Step 6: Measuring functional titer. For measurements of functional titer, undiluted samples of AAV1, AAV2 and AAV5 produced using the cloned hybrids were infected at a range of dilutions and added to fixed population of un-infected HEK 293 cells. Functional titers were measured in transduction units (TU) per milliliter (mL). Infectivity was determined by quantifying percent fluorescent-positive cells by flow cytometry.

Step 7: Expand high producer clones. The original aliquots corresponding to samples that showed high levels of capsid production and functional titer were expanded to establish producer cell lines for transduction and expression of other types of viral vectors and particles.

Figure 10A:
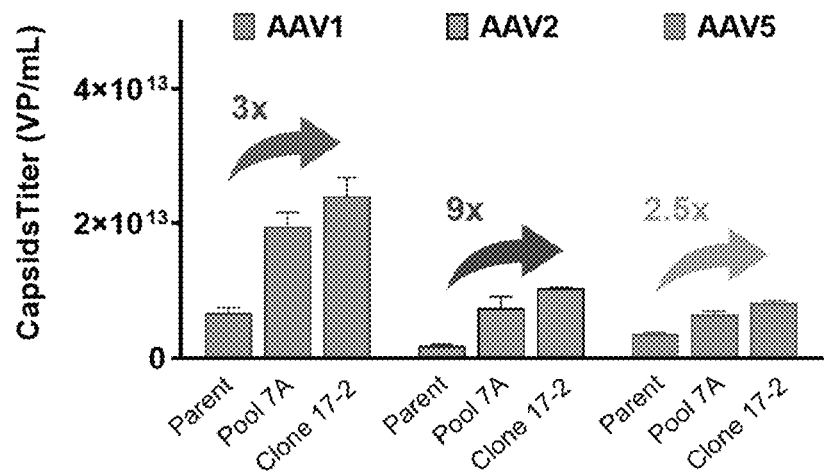
FIGS. 10A, 10B, and 10C demonstrate higher productivity of capsids of several serotypes of AAV vectors from fused HEK 293 cells. Engineered clone (17-2) showed 3-fold, 9-fold, and 2.5-fold increase of AAV vectors compared with parent host, respectively.
Figure 10B:
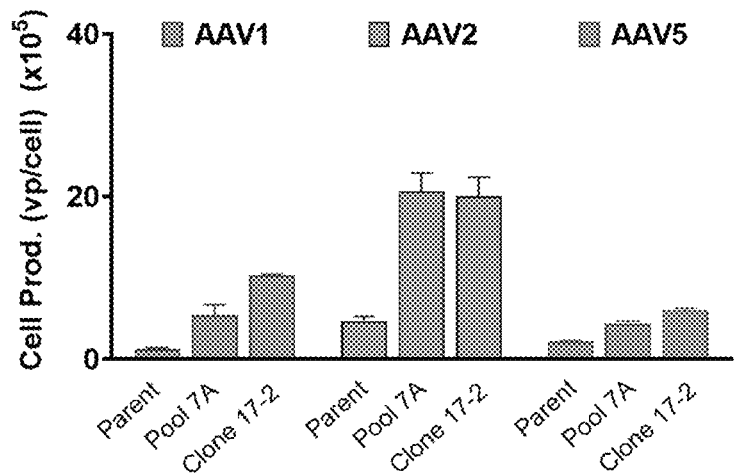
Figure 10C:
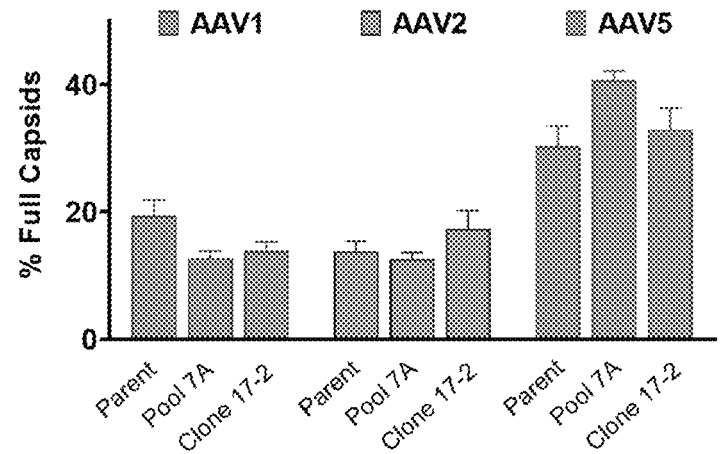

FIGS. 10A, 10B, and 10C demonstrate higher productivity from cells fused, cloned, and sampled according to this illustration. Host cells were transiently transfected with (1) transfer plasmid expressing fluorescent reporter; (2) packaging plasmid expressing Rep and Cap proteins specific for AAV1, AAV2, or AAV5; and (3) helper plasmid. Capsid concentration or titer were measured by biolayer interferometry (BLI) using a biosensor that binds to AAV1, AAV2, or AAV5 capsids. Cumulative capsids productivity (FIG. 10A), cell specific productivity (VP/cell) (FIG. 10B), and percent full capsids (FIG. 10C) of AAV1, AAV2, AAV5 of HEK 293 parent, engineered pool (7A) and clone (#17-2). Engineered clone (17-2) showed 3-fold, 9-fold, and 2.5-fold increase compared with parent host, respectively.

Figure 11A:
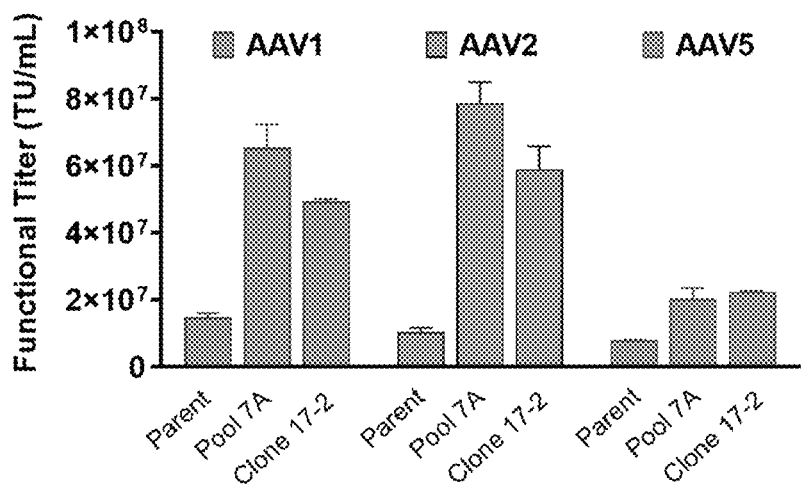
FIGS. 11A and 11B. demonstrate higher functional titer of several serotypes and other features of AAV vectors from fused HEK 293 cells.
Figure 11B:
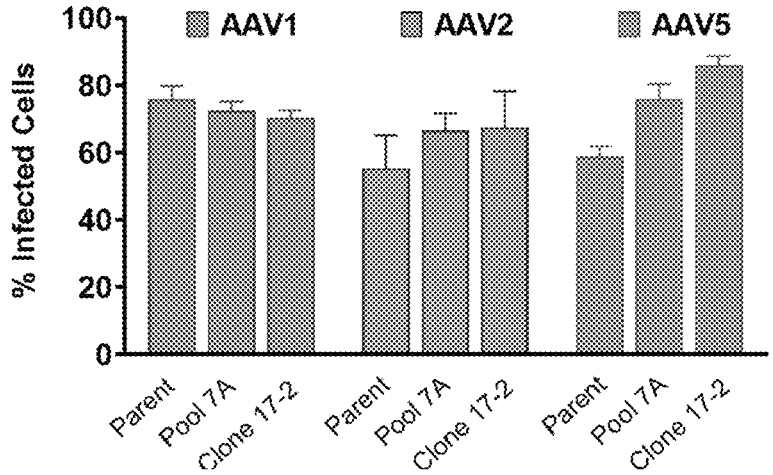

FIGS. 11A and 11B. demonstrate higher functional titer from cells fused, cloned, and sampled according to this illustration. Concentrated packaged AAV1, AAV2, and AAV5 virus were infected in HEK 293T cells at different multiplicity of infection (MOI) and percent infected cells were determined by gating for fluorescent-positive cells using flow cytometry. FIG. 10A: Mean functional titer were calculated at three different virus concentrations (dilutions ranging from 1:25 to 1:300). FIG. 10B: Cell infectivity measured by % cells exhibiting GFP fluorescence (AAV transfer vector transgene) at 3 different multiplicity of infection (MOI) ranging from 500 to 50,000 (serotype dependent).

Figure 12:
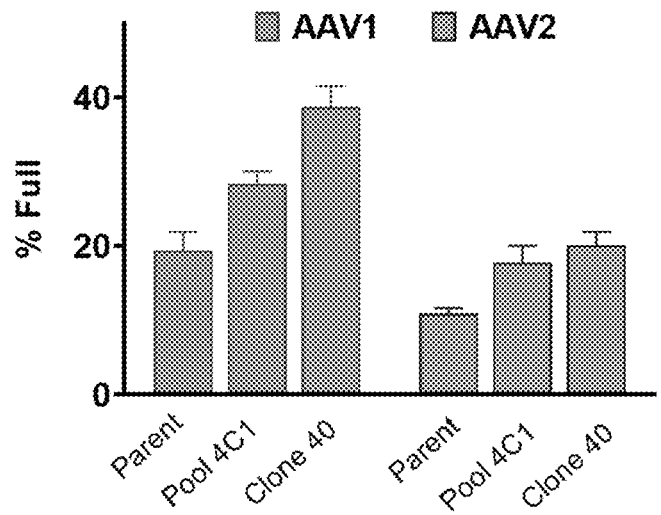
FIG. 12 demonstrate an improvement in the proportion of capsids containing a nucleic acid payload achieved by screening fused cells for cell phenotype. Engineered HEK 293T pool (4C1) clone (#40) selected for high mitochondria (top 10%) and high reactive oxygen species (top 10%) showed a two-fold increase in full-to-empty ratio for the AAV2 serotype

FIG. 12 demonstrate an improvement in the proportion of capsids containing a nucleic acid payload achieved in this illustration. Host cells were transiently transfected with transfer plasmid expressing fluorescent reporter; packaging plasmid expressing Rep and Cap proteins specific for AAV1 or AAV2; and helper plasmid. Full-to-empty ratio of AAV1 and AAV2 of lysed cells were measured by BLI. Engineered HEK 293T pool (4C1) clone (#40) selected for high mitochondria (top 10%) and high reactive oxygen species (top 10%) showed a two-fold increase in full-to-empty ratio.

7. Making Cell Hybrids

Individual high producer cells can be selected from any cell population that is heterogeneous in this respect, as described in the section that follows. Many single cell lines (such as CHO and HEK-293 cells) are sufficiently diverse at the outset in terms of gene content and intracellular apparatus in the proliferating cell population that they can be sorted and selected for high producer cells directly from a standard culture.

Optionally, to improve final product yield or enhance the sorting process, the user may prepare cells for sorting by taking one or a combination of techniques that will either enhance heterogeneity of levels of virus production within the cell population, or generally increase the levels of virus production for the cells population as a whole, or a subpopulation thereof. Suitable techniques are those that alter the genome of the cells, for example, to shuffle the genome and increase copy numbers of that contribute to the intracellular machinery involved in virus production or assembly. Altering or shuffling the genome in this manner may yield many genetic variants with one or more of a variety of different properties, including levels of virus production and growth rate.

The technology of this disclosure is based on part on the disclosure that cells suitable for virus production can attain a higher level of production by fusing with other cells. Without limiting practice of the invention, it is hypothesized that fusing two cells together is partly additive in terms of the components, genetics, or genetic control of the cells that participate in virus production. It is beneficial if the improved characteristics breed true. Accordingly, after cells are fused, they are typically subject to multiple rounds of culturing and selection for phenotypic characteristics of interest. The resulting cells may be aneuploid or otherwise retain all or part of the genomes of parental cells that encode cell components involved in virus production.

Model cells suitable for fusion are cell lines that have already been employed for industrial virus production, such as CHO cells, mouse myeloma NS0 cells, mouse myeloma SP2/0 cells, rat myeloma YB2/0 cells, Human Embryonic Kidney (HEK) 293 cells, HeLa, Per.C6, HT-1080, Huh-7, Baby Hamster Kidney (BHK-21), and Per-CP cells. In the context of this disclosure, a "cell line" is a population of cells that can be propagated continually, extensively, or indefinitely in tissue culture. A starting cell line is typically heterogeneous in terms of one or more phenotypic features that relate to the amount of gene product from a transgene that the cell will produce. When cultured, a producer cell line obtained according to this disclosure may produce progeny that are heterogeneous, substantially homogeneous, or clonal.

Cell fusion is performed by obtaining a cell mixture of cells to be fused: (a plurality of cells from one cell line, or more than one cell line, or a mixture of at least one cell line and at least one primary cell population. The cell mixture is then subjected to an appropriate fusion protocol: for example, by culturing under culture conditions that promote the formation of hybrids, by conducting an electrofusion, by combining with a fusogenic virus such as Sendai virus, by placing cells into contact (for example, by gentle centrifugation), by treating with a fusogenic agent such as polyethylene glycol (PEG), or using any effective combination thereof.

For purposes of this disclosure, cells that have been made by fusing two or more cells together may be referred to as autotypic hybrids (cells from the same cell line fused together), isotypic hybrids (cells having the same genotype), allotypic hybrids (cells from different individuals of the same species having different genotypes), and xenotypic hybrids (cells from different species). Autotypic hybrids are typically formed using a population of cells that consists essentially (that is, at least 99%) of cells from a single cell line. The other types of hybrids are typically formed using cell populations from two or more cell lines which have potentially complementary properties. The disclosure also includes the fusion of one or more cell populations isolated or obtained from primary sources with themselves or with established or cloned cell lines.

Cells may be fused into hybrids using any suitable technique. For example, cells may be cultured in the presence of a fusogenic agent and/or under culture conditions that promote the formation of hybrids, or may be forced into contact, for example, by gentle centrifugation, optionally in combination with a fusogenic agent such as polyethylene glycol (PEG). Typically, a fused cell is obtained by fusing two cells together, although fusion of three or more cells is possible. It is recognized that fusion of two different cell populations will result in mixed cell products (isotopic, allotypic, or xenotypic hybrids, depending on the parental cell lines), and autotypic hybrids. Autotypic or isotopic hybrids can be separated from allotypic or xenotypic hybrids, if desired, using fluorescently labeled or surface bound antibody specific for a ligand expressed on one of the cell lines in the mixture, but not another.

All such combinations come within the scope of this invention, unless explicitly indicated otherwise. It may be beneficial to repeat the cell fusion within a population of hybrids to enhance the effect further, and/or cross-hybridize with other cell lines to imbue the ultimate cell line with additional beneficial characteristics. Thus, the fusion and selection steps may be done iteratively twice, three or four times, or more.

8. Selecting High Producer Cell Lines and Preferred Phenotypic Features

This disclosure provides a variety of means for identifying and selecting cell hybrids that have the capacity of generating high producer cell lines. Cells can be transfected with a reporter gene (for example, genes that encode fluorogenic products such as green florescent protein), along with genes that encode a viral capsid for testing purposes. High producers can be selected on the basis of viral capsids produced and/or encapsulated promoter gene products.

Alternatively or in addition, cell hybrids can be selected for characteristic phenotypes that correlate generally with high levels of protein and/or virus product. A valuable insight that underlies this technology is the idea that the production of biological agents can be increased by selecting cells from a mixed cell population for optimal levels subcellular machinery or biochemistry that support increased virus production, compared with other hybrids or parental cells in the starting mixture.

Such phenotypic features include the relative density of subcellular organelles, particularly those involved in secretion of protein or viral particles from the host cell, and the relative level or concentration of enzymes that help finish or assemble viruses. These include mitochondria, peroxisomes, endoplasmic reticulum, Golgi, and nucleoli. Such phenotypic features also include aspects of the cell cytosol or cell contents generally, such as reactive oxygen species, redox carrying molecules, and pH.

Depending on the viral system being optimized, it may be preferrable to have higher or lower levels of any of such phenotypic features, either alone or in combination. As part of the initial aliquoting or cloning step, cells can be stained with an appropriate vital dye, and separated using a cell sorter or other means into aliquots that are low (the least 10%, or the last 5% to 25%), medium (the middle 30% to 70%), or high (the greatest 10%, or the greatest 5% to 25%) in each of the features on a per-cell basis. Hybrid cells falling within any or all of these ranges can be recovered and aliquoted or cloned, then tested for virus production and effective titer. Ranges that are determined to confer an advantage can then be used as additional criteria for finding other high producer aliquots or clones for related viral serotypes or systems.

The makers of this invention have discovered that fused cells sorted for higher mitochondria content and higher levels of reactive oxygen species (ROS) can be used to make producer cells that generate viral capsids that are as much as two-fold higher in the proportion of capsids that contain an intended pharmaceutical payload, such as a polynucleotide for purposes of gene therapy or vaccination.

9. Selecting for Cellular Content of Mitochondria

Many viral proteins localize to the mitochondrion. Mitochondria content and function are used as basis for sorting or selection without damaging the cell using vital dyes. Such dyes can be obtained commercially, for example from the companies: Invitrogen and Sigma Aldrich. Example of vital dyes for the mitochondria include: MitoTracker Green FM; MitoTracker Orange CMTMRos; MitoTracker Red CMXRos; MitoTracker Red FM; MitoTracker Deep Red FM; BioTracker 488 Green Mitochondria dye; BioTracker 633 Red Mitochondria dye; BioTracker 405; and Blue Mitochondria.

Functional dyes to measure the membrane or redox potential of the mitochondria can also be used to sort or select for cells with enhanced mitochondria function. Mitochondria potential is generated by Complexes I, III and IV and serves as a reliable read-out to assess mitochondria function. Membrane depolarization shifts fluorescence signal from one wavelength to another. These membrane potential dyes are available from companies: Invitrogen and Sigma Aldrich: JC-1 Dye (Invitrogen T3168; Sigma CS0390); JC-9 Dye (Invitrogen D-22421); and C10 Dye (Sigma MAK160, MAK159).

Additional characteristics to sort for enhanced mitochondria includes vital dyes to measure mitochondria calcium, superoxide production, and dyes selective to the mitochondria. These include: Rhod-2 AM Reagent (Invitrogen R1245MP); and MitoSOX Red (Invitrogen M36008).

Alternatively or in addition, the user can test expression-based labeling systems that would introduce a fluorescent protein targeted to the mitochondria. They are fusion proteins comprising a portion that expresses an optical label, fused with a protein sequence that targets or is processed by the organelle to be labeled. Examples include the following. From Invitrogen: CellLight™ Mitochondria-GFP (C10600); and CellLight™ Mitochondria-RFP (C10505, C10601). From Evrogen: pTagCFP-mito (FP117); pTagYFP-mito (FP137); pTagRFP-mito (FP147); pmKate-mito (FP187); pTagGFP2-mito (FP197); pTurboRFP-mito (FP237); pTurboGFP-mito (FP517); pPhi-Yellow-mito (FP607); and pTurboFP602-mito (FP717). From Takara Bio: pAcGFP1-Mito Vector (632432); pDsRed2-Mito Vector (632421); pHcRed1-Mito Vector (632434); and pPAmCherry-Mito Vector (632591);

After staining with any of these dyes, cells may be selected (for example, by flow cytometry and sorting) that have on average a level of staining that is at least 1.2, 1.5, 2, or more than 2-fold higher than the parental cell line or lines, in terms of staining, for example, for mitochondria or an optically labeled gene product.

10. Selecting for Cellular Content of Peroxisomes, Reactive Oxygen Species, and pH Peroxisomes are plastic subcellular organelles found in nearly all eukaryotes. They serve as the cell's external sensors, functioning as hubs for reactive oxygen species (ROS), lipids and amino acid β-oxidation (reviewed in Smith and Aitchison, 2014). Peroxisomes can be labeled with expression-based labeling, in which a fluorescent protein would be targeted to peroxisome using peroxisomal targeting sequence.

Examples include the following: CellLight™ Peroxisome-GFP, BacMam 2.0 (Invitrogen, C10604); pmKate2-peroxi (Evrogen, FP313); and pPhi-Yellow-peroxi-peroxi (Evrogen, FP606).

After staining with any of these dyes, cells may be selected (for example, by flow cytometry and sorting) that have on average a level of staining that is at least 1.2, 1.5, 2, or more than 2-fold higher than the parental cell line or lines, in terms of staining, for example, for peroxisomes or an optically labeled gene product.

This disclosure demonstrates for the first time that increased cellular content of ROS correlates with enhanced viral production. Reactive oxygen species (ROS), such as superoxide anion ($O^{2-}$), hydrogen peroxide ($H_2O_2$), and hydroxy radical (HO•), constitute radical and non-radical oxygen species formed by partial reduction of oxygen. Cellular ROS are generated endogenously as in the process of mitochondria oxidative phosphorylation and have been implicated in a variety of pathological diseases such as cancer, neurodegeneration, and aging.

Cellular reactive oxygen species can be measured using fluorescent probes, wherein upon oxidation, these reagents exhibit strong fluorescence and remain localized within the cell. These dyes are commercially available and include the following: From ThermoFisher: CellROX® Green; CellROX® Orange; CellROX® Deep Red; and H2DCFDA. From Abcam: DHE (Dihydroethidium) Assay Kit.

Intracellular redox levels can be determined using Oxy-BURST Green reagents, RedoxSensor Red CC-1 stain, and reduced calcein, ethidium, fluoresceins, MitoTraker probes, and rhodamines. Intracellular pH can be determined using 9-amino-6-chloro-2-methoxyacridine (ACME), BCECF indiator, dextran conjugates, fluorescein and fluorescein derivatives, 8-hydroxypyrene-1,3,6-trisulfonic acid (HPTS), LysoSensor probes, Oregon Green dyes, pHrodo indiator, SNARF indicator, and thiol-reactive pH indicators.

11. Selecting for Levels of Other Intracellular Organelles

Alternatively or in addition, high producer cells can be identified or selected according to intracellular content of other organelles.

Selecting for endoplasmic reticulum (ER) and/or Golgi apparatus. These organelles play a central role in protein production. Either or both of these can be measured and used as a basis for sorting or selection without damaging the cell using a vital dye, and the cells can be selected on the basis of the amount of dye that is associated.

Such dyes can be obtained commercially, for example from the company Molecular Probes. Examples of vital dyes for ER include: ER-Tracker™ Blue-White DPX (E12353); ER Tracker™ Green (glibenclamide BODIPY® FL) (E34251); ER-Tracker™ Red (glibenclamide BODIPY® TR) (34250); $DiOC_6$ (D273); and $DiOC_5$ (D272). Vital dies for Golgi apparatus include NBD C6-6-ceramide (N1154); NBD C6-sphingomyelin; BODIPY® FL C5-cerimide (D3521); and BODIPY® TR ceramide (D7540).

Alternatively or in addition, the user can test expression-based labeling systems that would introduce a fluorescent protein targeted to ER or Golgi. They are fusion proteins comprising a portion that expresses an optical label, fused with a protein sequence that targets or is processed by the organelle to be labeled. Examples include the following: From Invitrogen: CellLight™ ER-GFP (C10590); Cell-Light™ ER-GFP (C10591); CellLight™ Golgi-GFP (C10592); CellLight™ Golgi-GFP (C10593). From Evrogen: pmKate2-ER (FP324); pFusionRed-ER (FP420); pTagRFP-Golgi (FP367); pTagRFP-Golgi (FP367); and pFusionRed-Golgi (FP419). From Clontech: pDsRed2-ER Vector (632409); pDsRed-Monomer-Golgi Vector (632480); and pAcGFP1-Golgi Vector (632464).

After staining with any of these dyes, cells may be selected (for example, by flow cytometry and sorting) that have on average a level of staining that is at least 1.2, 1.5, 2, or more than 2-fold higher than the parental cell line or lines, in terms of staining, for example, for ER, Golgi, or an optically labeled gene product.

Selecting for high cellular content of nucleoli. The nucleolus is the largest subnuclear organelle in the cell where ribosomal RNA are assembled and transported to the cytoplasm and support the protein translational machinery. Nucleoli can be labeled in a cell by vital dyes. Fluorescent probes targeting ribosomal RNA can also be used to selectively stain for this suborganelle. Examples include the following: Nucleolar Staining Kit (Abcam, ab139475); NUCLEOLAR-ID Green Detection Kit (Enzo Life Sciences, 51009-500); and SYTO RNASelect Green (Invitrogen, S32703).

After staining with any of these dyes, cells may be selected (for example, by flow cytometry and sorting) that have on average a level of staining that is at least 1.2, 1.5, 2, or more than 2-fold higher than the parental cell line or lines, in terms of staining, for example, for nucleoli or an optically labeled gene product.

12. Characterizing High Producer Cell Lines

Cell hybrid cells that have been optimized for the production of viral vectors and particles can be characterized by one or more criteria in any combination.

Suitable criteria include cell karyotype. Chromosome patterns can be characteristic of homotypic and heterotypic cell fusions. The following characteristics may be favorable for virus production:
- duplication of chromosomal segments
- loss of chromosomal segments (90%, 80%, 70%, 60% or less than 50% of original segment size)
- differences in heterochromatin distribution and amounts (differences of 10%, 20% or greater than 20% and/or distribution differences of heterochromatin greater than 20%)
- translocation events (2 or more translocation events on the same or different chromosome segment compared to parental cell line)

Producer cells can also be characterized on the basis of cell phenotype, such as intracellular content of mitochondria, peroxisomes, reactive oxygen species (ROS), endoplasmic reticulum, Golgi apparatus, nucleoli, and so on, using the materials provided above.

13. Determining Production Capacity and Characteristics of Producer Cells

A cell line or mixed cell population that has been selected for high levels of virus production may be characterized in comparison with the parental or originating cell line by any one or more of several different parameters. For example, the selected cells may have: (1) a genome that is more aneuploid than the starting cells, containing part or all of the genome of two or more parental cell lines (which may or may not be the same), (2) a higher concentration of mitochondria, peroxisomes, endoplasmic reticulum, Golgi apparatus, reactive oxygen species, or other phenotypic feature compared with any one or all of the parental cell lines (for example, between 2 to 5-fold or 4 to 8 fold, or more than 2-, 4-, or 8-fold higher), (3) a capacity to produce a level of virus per cell or per liter of culture fluid that is substantially higher than the parental cell line (for example, between 2 to 5-fold or 4 to 8 fold, or more than 2-, 4-, or 8-fold higher), (4) a capacity to produce a particular amount of virus per cell (for example, more than 50, 65, 75, 100, 150, 200, 300, 500, 2000, 5000, or 20,000 capsids per cell; (5) a capacity to produce a certain amount of virus per volume of culture fluid (for example, at least 5, 8, 12, 20, or 30 grams, or between 8 and 20 or between 10 and 50 grams of virus per liter of culture fluid; or (6) a capacity to produce viral vectors or particles that have a higher proportion of payload-carrying capsids (50% higher, or 2 or 3-fold).

For the purpose of making such comparisons, the producer cell line can be compared with a standardized population of the original cell line, either kept on hand, as part of the same system, or obtained from a reference source. For example, CHO derived producer cells may be compared with CRL-12023 cells from the American Type Culture Collection (ATCC®). This disclosure includes systems for high-level production of virus-based pharmaceuticals, comprising both a starting cell line, and a producer cell line derived therefrom that has a relatively high density of mitochondria and/or reactive oxygen species per cell, as determined, for example, using one or more of the vital dyes listed above.

14. Genetically Altering Producer Cells to Synthesize and Produce Viral Elements To generate a cell line expressing viral gene products, producer cells or their precursors can be transfected with a single gene encoding viral elements such as proteins and nucleic acids. More often, the viral elements are introduced into a host cell using multiple vectors.

The expression of the gene cassette(s) can be under control of following combinations of mammalian promoters: ubiquitous, endogenous viral promoters (not ubiquitous, e.g. p5 and p19), hybrid promoters, and/or inducible promoters that cause expression of single or multiple gene cassette(s) in the host cell line. The gene can be placed in forward or reverse orientation with respect to the promoter. The gene or plurality of genes can be flanked by recombination sites (FRT and its variants; and/or lox and its variants). These recombination site variants include: loxP, lox511, lox2272, FRT or mFRT71. Site specific recombinases such as Cre or Flippase is expressed in the same cell to allow for site-specific recombination and change the orientation of the gene from reverse to forward.

For example, the recombinase can be expressed by transient transfection wherein the gene encoding for the recombinase is under the control of ubiquitous or inducible mammalian promoter. In another illustration, purified recombinase protein or mRNA can be transfected into the cell. In another illustration, the recombinase can be delivered using adenovirus, lentiviruses, AAV, Moloney Murine Leukemia Virus (MMLV), Murine Stem Cell Virus (MSCV), Vesicular Stomatitis Viruses (VSV), or Herpes Simplex Viruses (HSV). Multiple genes can be expressed by the same promoter through the use of polycistronic elements such as T2A, P2A, E2A, F2A, IRES and IRES2 elements. Inducible promoters result in expression of gene or gene cassette upon addition of a stimulus, that can be chemical (e.g. doxycycline, tetracycline, cumate, recombinase such as Cre or Flippase) or physical (e.g. blue light). The level of production of the target protein can be determined in the course of processing using a transient transfection method to insert a gene expression cassette.

Alternatively or subsequently, permanent transfection can be done that integrates the gene of interest and/or a marker gene into the genome of the cell line. Multiple copies of gene integration (as much as fifty of integrated copies per cell) can be achieved by co-transfection of transposase and gene cassette flanked by transposase recognition sites known as transposase inverted terminal repeats.

Adenovirus, adeno-associated viruses (AAV), and lentiviruses can be produced by transient transfection of one or more combinations of the following vectors into a cell line: helper, packaging, envelope, and/or transfer vectors. Gene cassette for helper, packaging, envelope and transfer vectors differ depending on the type of virus produced. Helper vector can express E2A and E4 genes as well as the VA RNA for adenovirus and AAV. In another illustration, packaging vector expresses Rep and Cap genes for adenovirus and AAV while a different packaging vector expresses Gag, Pol, Rev and its response elements for lentivirus production Alternatively, Rep or envelope genes can be expressed in an inducible manner wherein Rep gene cassette is split in two segments (5' and 3' segment) and these two segments are joined by stop cassette, containing transcription termination and polyadenylation sequences flanked by two homologous recombination sites, located in cis. In another preferred illustration, E2, E4 and VA cassette is placed under the control of an inducible promoter in the reverse orientation with respect to the promoter. Activation of EEV is achieved through delivery of Cre and Doxycycline. In a preferred illustration, loxP and lox511 is used to recombination Other heterologous recombination sites can be used: lox2272, FRT, and mFRT71. In the case that any combination of FRT and mFRT71 recombination sites are used, Flippase must also be delivered to the cell. Envelope vector is only required for production of lentiviruses not adenovirus or AAV. Transfer vectors backbone containing gene of interest is unique to virus type. Lentivirus transfer vectors backbone consists of: 5' and 3' LTR, Psi packaging signal, and Woodchuck Hepatitis Virus Posttranscriptional Regulatory Element (WPRE). Adenovirus and AAV transfer vector backbone contain inverted terminal repeats flanking promoter, gene of interest, and WPRE.

Adenovirus or AAV can be produced by transfection of helper, packaging, transfer vectors into a cell line which does not contain integrated copies of any of the viral vectors. In another illustration, transfer vector (expressing gene of interest) is transfected in a cell line containing stable integration of helper and packaging elements. In another illustration, the cell line may have stable integration of helper, packaging and transfer vectors.

Lentivirus can be produced by transfection of packaging, envelope, and transfer vectors into a parental host cell line. In another illustration, lentivirus is produced by transfection of transfer vector (expressing gene of interest) into a cell line containing stable integration of helper and packaging elements. In another illustration, virus is produced in the cell line with stable integration of helper, packaging and transfer vectors.

Transfection can be done using liposome-based reagents (for example, Lipofectamine™ 3000, Expifectamine 293, FuGENE™ HD, X-Fect nanoparticles polymer, Trans-IT Pro reagents, Trans-IT VirusGen, polyethylenimine), calcium phosphate, electroporation, or infection with an adenovirus, retrovirus or lentivirus-based vector.

Following transfection, the cells are tested for production for packaging of the intended virus: for example, by enzyme-linked immunosorbent assay (ELISA), quantitative real-time PCR (qPCR), or biolayer interferometry (BLI). Cells or clones having increased production of the desired virus are selected. The objective can be an increase in virus production that is 1.5, 2, 4, 8, 12, 16, 20, or 100-fold higher than the parental cell line; and/or production at a level of greater than 1012 viral genome/ml or capsids/ml for AAV; and/or greater than 108 infectious units (IFU) per ml of culture fluid under typical manufacturing conditions. The virus of interest can also be tested for other desired characteristics, such as full to empty capsid ratio and functional titer.

In principle, the transfection can be done either before, during, or after one or more cycles of fusion and selection for other features. For example, the fusion and selection can be done before transfection with the packaging, helper and transfer vector containing gene of interest, thereby establishing a parental cell line suitable for high-level of virus production of the user's choice. Alternatively, the transfection can be done into the originating parental cell line containing gene(s) of interest and used to track production levels during subsequent fusion and sorting steps, or to provide another basis for such sorting. Alternatively, the transfection can be done as an intermediate step, wherein the cells have already been subject to one or more cycles of fusion and selection for some other feature such as ER, Golgi, mitochondria, peroxisomes, nucleoli or other proteins (referred to earlier in this disclosure). The resulting hybrid is transfected to express virus of interest, and then subjected to further cycles of fusion and selection for expression of the virus of interest and/or other features referred to earlier in this disclosure.

Another option is to develop a cell line using a reporter gene as a proxy for the virus payload that ultimately will be manufactured: for example, secreted alkaline phosphatase, secreted luciferase, fluorescent virus payloads such as red fluorescent virus payload or green fluorescent virus payload. Again, the transfection can be done before, during, or after multiple cycles of fusion and selection, optionally using the level of expression of the marker as the selection criteria in one or more of the cycles. This creates a parental cell line that is optimized for expression of the marker virus payload, with the expectation that the beneficial characteristics of the cell line will be retained after further genetic alteration to produce a biological product of commercial interest.

Ultimately, once a cell line has been developed having a desired level of expression of the marker virus payload, the marker is then replaced with the virus payload of interest. Transfection can again be done randomly into the genome, using the techniques listed above, and expression of the reporter gene is curtailed. Alternatively, the gene for the reporter gene can be substituted with a gene that encodes the virus payload of interest using a targeted integration technique. Such techniques comprise, for example, CRISPR/Cas virus payloads, CRISPR/Cas associated transposase (CASTs), recombinase cassette exchange (RMCE), a zinc-finger recombinase (ZFR), or a transcription activator-like effector nuclease (TALEN). That way, the gene of interest is inserted into the genome of the cells from the producer cell line or the mixture at a location that is pre-selected as permitting or supporting a high level of transcription, compared with other locations in the genome.

15. How to Use Transposases for Stable Transfection of Producer Cells

Transposons are DNA sequences that can move one position of the DNA via (1) copy and paste or (2) cut- and paste mechanisms. They have recently emerged as promising molecular biology toolkits for gene amplification where as much as 50 copies can be introduced into the genome. Compared to transposons, traditional transfection techniques using chemical-based methods or electrical currents can only integrate single or very few copies of transgene into the host genome.

By way of illustration, a Class II transposon, "Sleeping Beauty" may be used to stably introduce multiple copies of viral genes into the cells. By predictably introducing desired copy numbers of specific viral genes stably into the cell, benefits of maximizing viral production can be realized. The optimal ratio of viral proteins is critical for proper packaging of lentiviruses, adenoviruses and AAV and can vary depending on the type of virus. The idea of the use of Class II transposon (Sleeping Beauty and PiggyBac to amplify copy numbers of integrated viral genes into the cell can also be applied to Class I transposons and CRISPR transposons (CASTs; Mougaikos and Beisel, 2021).

The multi-component molecular systems such as SunTag system can be used to amplify gene expression of viral genes in a cell line without the use of Sleeping Beauty transposase system. Global transcription factors such as Tat or p300 are tagged with multiple copies SunTag scaffold containing multiple copies of GCN4 epitope. Cognate scFv fragment are fused to heterotypic fusion protein consisting of the transactivation domains: p53, VP64, p65, and Rta (SSPVP), see FIG. 3). When these components are co-expressed in the cell, hereby called super transcriptional activation complexes (STAC), this can result in amplified gene expression of the viral genes in a synergistic manner. In contrast to amplified gene copies using transposase system, benefits of amplified gene expression for cells containing few gene copies integrated can be realized using such systems. This would allow for amplification beyond the normal level of endogenous biological systems.

16. Suitable Viral Strains for Use in Therapy

The technology of this disclosure can be implemented in any viral strain selected by the user, mutatis mutandis. TABLE 1 provides some examples of viral gene elements that can be transfected into the producer cell lines of this disclosure for preparation of lentivirus, adenovirus, and AAV vectors.

TABLE 1

List of viral types and elements transfected into the producer cells.

| Element | Virus Type | Inducible | Reason |
|---|---|---|---|
| Gag-Pol, RRE | Lentivirus | no | |
| Tat | Lentivirus | no | |
| Rev | Lentivirus | no | |
| VSV-G | Lentivirus | yes | ratio of envelope protein, VSV-G to Gag-Pol needs to be controlled |
| VP1 | Adeno/AAV | no | |
| VP2 | Adeno/AAV | no | |
| VP3 | Adeno/AAV | no | |
| Rep78 | Adeno/AAV | yes | cytoxic |
| Rep68 | Adeno/AAV | yes | cytoxic |
| Rep52 | Adeno/AAV | no | |
| Rep40 | Adeno/AAV | no | |
| E2A | Adeno/AAV | yes | high concentration results in cell death |
| E4 | Adeno/AAV | yes | high concentration results in cell death |
| VA | Adeno/AAV | yes | high concentration results in cell death |

17. Promoters for Expressing Viral Gene Elements Stably Transfected into Producer Cell Lines If a producer cell line is stably transfected to integrate viral transgenes into the cell's genome, it is sometimes helpful in the regulation of such cells if the promoters used to drive the expression of viral genes in producers cells are inducible.

An example is the cumate inducible promoter (CymR), a repressor that binds to the cumate operator sequences (CuO) in the absence of Cumate. In presence of cumate, Cumate binds to CymR allowing for activation of gene downstream of CuO. U.S. Pat. Nos. 8,728,759 and 7,745,592 B2. Also suitable are tetracycline response elements (TRE), which can be induced using doxycycline or tetracycline. Light inducible promoters can also be used, such as the blue light inducible promoter from GenTarget, Inc.

18. Methods for Quantifying Levels of Viral Production from Cell Hybrids

Real-time quantitative PCR measures viral transcription, concentration of viral genome (vg/ml). Each viral particle typically contains one viral genome. Viruses are treated with Dnase I to remove any of the host genomic DNA. Primers binding to targeted regions in the transfer vector are used and amplicon is detected by either probe-based method or SYBR Green, which binds to the amplicon.

Indirect ELISA and biolayer interferometry (BLI) are used to measure total capsid AAV particles. These measurements utilize an antibody against an abundant capsid protein present in AAV serotype. Samples are captured by capsid antibody and detected using biotinylated capsid antibody and Streptavidin conjugated to HRP for chemiluminescent detection.

For lentivirus, infectious particles can be measured by indirect or sandwich ELISA using antibody to p24. Anti-p24 is used to capture samples and detected using biotinylated anti-p24 along with Streptavidin conjugated to HRP for chemiluminescent detection.

Functional titer or infectious titer of viruses is the concentration of viral particles that can transduce cells. Functional titer can be measured by cell transduction using a fluorescent or chemiluminescent protein as a reporter. Cell lines are infected or transduced with packaged viruses at specific multiplicity of infections (MOI). % of cells expressing reporter gene are quantified and correlated with the # of virus particles used to transduce cells.

19. Pharmaceutical Payloads and Therapeutic Applications

Viral vectors and particles produced according to this disclosure can be used for delivering a variety of pharmaceutical payloads to human subjects in need thereof. Suitable are proteins and nucleic acids of various kinds, or a combination thereof. Treatment is done by administering to a subject an amount of the vector or particle that is effective in achieving one or more clinical aims.

The technology of this disclosure is advantageous for delivering a nucleic acid, a protein, or mixture thereof for purposes of inducing a specific immunological response. Illustrative payloads for immunogenic compositions or vaccines are shown in TABLE 2. The packaged nucleic acid encodes one or more epitopes from the intended immune target, and optionally one or more additional proteins that may act as an adjuvant or stimulant to enhance immunogenicity. The target may be an infectious agent, such as a pathogenic virus, bacteria, or protozoan. Alternatively, the target may be a cancer cell, in which case the encoded epitopes are epitopes expressed by the cancer cell that are specific to the cancer or to the tissue type.

For example, the technology of this disclosure can be used to prepare a composition to induce a response to the SARS-CoV-2 virus, for the purpose of prevention or treatment of COVID-19. Representative immunogenic epitopes may be taken from any one or more of the four SARS-CoV-2 structural proteins: namely, membrane glycoprotein (M), envelope protein (E), nucleocapsid protein (N), and the spike protein (S). Most current vaccines against SARS-CoV-2 typically include or encode the whole spike protein. Ways to optimize the spike protein were recently discussed by F. Heinz & K. Stiasny, NPJ Vaccines (2021) 6:104.

TABLE 2

| Immunogenic payloads for viral vectors and particles | | | | |
|---|---|---|---|---|
| Name | Disease | Encoded antigen | Clinical Trials identifier | Phase |
| Infections | | | | |
| mRNA-1273 | SARS-CoV-2 | Spike | NCT04470427 | III (EUA and CMA) |
| BNT162b2 | SARS-CoV-2 | Spike | NCT04368728 | III (EUA and CMA) |
| CVnCoV | SARS-CoV-2 | Spike | NCT04652102 | III |
| LNP-nCoVsaRNA | SARS-CoV-2 | Spike | ISRCTN17072692 | I |
| ARCT-021 | SARS-CoV-2 | Spike | NCT04728347 | II |
| ARCoV | SARS-CoV-2 | Receptor-binding domain | ChiCTR2000034112 | I |
| mRNA-1440 | Influenza H10N8 | Haemagglutinin | NCT03076385 | I |
| mRNA-1851 | Influenza H7N9 | Haemagglutinin | NCT03345043 | I |
| mRNA-1893 | Zika virus | Pre-membrane and envelope glycoproteins | NCT04064905 | I |
| mRNA-1345 | Respiratory syncytial virus | Fglycoprotein | NCT04528719 | I |
| mRNA-1653 | Metapneumovirus and parainfluenza virus type 3 (MPV/PIV3) | MPV and PIV3 F glycoproteins | NCT03392389 | I |
| mRNA-1647 | Cytomegalovirus | Pentameric complex and B glycoprotein | NCT04232280 | II |

TABLE 2-continued

Immunogenic payloads for viral vectors and particles

| Name | Disease | Encoded antigen | Clinical Trials identifier | Phase |
|---|---|---|---|---|
| mRNA-1388 | Chikungunya virus | Chikungunya virus antigens | NCT03325075 | I |
| CV7202 | Rabies virus | G glycoprotein | NCT03713086 | I |
| Cancer | | | | |
| mRNA-5671/ V941 | Non-small-cell lung cancer, colorectal cancer, pancreatic adenocarcinoma | KRAS antigens | NCT03948763 | I |
| mRNA-4157 | Melanoma | Personalized neoantigens | NCT03897881 | II |
| mRNA-4650 | Gastrointestinal cancer | Personalized neoantigens | NCT03480152 | I/II |
| FixVac | Melanoma | NY-ESO-1, tyrosinase, MAGE-A3, TPTE | NCT02410733 | I |
| TNBC-MERIT | Triple-negative breast cancer | Personalized neoantigens | NCT02316457 | I |
| HARE-40 | HPV-positive cancers | HPV oncoproteins E6 and E7 | NCT03418480 | I/II |
| RO7198457 | Melanoma | Personalized neoantigens | NCT03815058 | II |
| W_ova1 | Ovarian cancer | Ovarian cancer antigens | NCT04163094 | I |

The technology of this disclosure can also be used for the purpose of gene therapy: for example, delivery of a nucleic acid encoding a gene product that is missing or defective in the subject being treated, or targeted to pathogenic cells in the subject, particularly cancer ells. Therapeutic purposes include but are not limited to expression of a therapeutic protein encoded in the nucleic acid (such as a cytokine or anti-cancer agent), expression of an essential protein that the subject is unable to produce themselves, or delivery of a gene editing system such as CRISPR/Cas9 or a guide RNA. Other possible therapeutic payloads may include DNA antisense oligonucleotides, DNA aptamers; micro RNAs, short interfering RNAs, ribozymes, RNA decoys and circular RNAs that specifically increase or decrease expression of a particular endogenous gene in the subject or an infectious agent. K. Sridharan et al., Br J Clin Pharmacol. 2016 September; 82(3): 659-672.

Illustrative payloads for gene therapy are shown in TABLE 3. In the examples shown, the nucleic acid encodes a therapeutic antibody (for passive immunization), anti-cancer drugs such as cytokines and chemotactic factors (for cancer treatment), and natural human proteins (to promote synthesis of an essential factor that the subject may be lacking, such as in the case of a genetically inherited condition). TABLES 2 and 3 are adapted from X. Hou et al., Nat Rev Materials 2021, 10:1-17.

TABLE 3

Nucleic acid sequences for gene therapy

| Name | Disease | Encoded protein | Clinical Trials identifier | Phase |
|---|---|---|---|---|
| Infections | | | | |
| mRNA-1944 | Chikungunya virus | Antibody against chikungunya virus | NCT03829384 | I |
| Cancer | | | | |
| mRNA 2416 | Solid tumors | OX40L | NCT03323398 | II |
| mRNA-2752 | Solid tumors | OX40L, IL-23 and IL-36γ | NCT03739931 | I |
| MEDI1191 | Solid tumors | IL-12 | NCT03946800 | I |
| SAR441000 | Solid tumors | IL-12sc, IL-15sushi, IFNα or GM-CSF | NCT03871348 | I |
| Genetic disorders | | | | |
| mRNA-3704 | Methylmalonic acidaemia | Methylmalonyl-CoA mutase | NCT03810690 | I/II |
| mRNA-3927 | Propionic acidaemia | Propionyl-CoA carboxylase | NCT04159103 | I/II |
| MRT5201 | Ornithine transcarbamylase deficiency | Ornithine transcarbamylase | NCT03767270 | I/II |
| MRT5005 | Cystic fibrosis | Cystic fibrosis transmembrane conductance regulator | NCT03375047 | I/II |

TABLE 3-continued

Nucleic acid sequences for gene therapy

| Name | Disease | Encoded protein | Clinical Trials identifier | Phase |
|---|---|---|---|---|
| NTLA-2001 | Transthyretin amyloidosis with polyneuropathy | CRISPR-Cas9 gene editing system | NCT04601051 | I |

20. Medicaments and Commercial Products

Preparation and formulation of pharmaceutical agents for use according to this disclosure can incorporate standard technology, as described, for example, in the most recent edition of *Remington: The Science and Practice of Pharmacy*. The formulation will typically be optimized for administration systemically, either intramuscularly or subcutaneously, or for administration orally or nasally (for example, to stimulate the mucosal immune system).

Preparations of viral vectors and particles may be provided as one or more unit doses (either combined or separate), each containing an amount of the pharmaceutical payload that is effective in the treatment of a chosen disease, infection, or clinical condition. The commercial product may contain a device such as a syringe for administration of the agent or composition in or around the target tissue of a subject in need thereof. The product may also contain or be accompanied by an informational package insert describing the use and attendant benefits of the vector or particle in treating the condition for which it is indicated and approved.

EXAMPLES

Example 1: Production of Protein by Cell Hybrids

In this example, CHO cells were fused and sorted for a high content of endoplasmic reticulum (ER) for the purpose of maximizing protein production.

CHO-K1 cells were exposed to a PEG-assisted fusion procedure. The cells were allowed to recover for one week, then the procedure was repeated for a total of three times. Following recovery from the third fusion, the cells were stained with vital ER-tracking dye (ER-Tracker™ Green (glibenclamide BODIPY® FL); Invitrogen, E34251) and sorted using a FACSAriaII™ cell sorter (BD Biosciences). Ten percent of the viable population exhibiting the highest amount of staining with ER-Tracker dye was collected. Following a two-week recovery in culture, the cells were exposed to a final fusion, stained with ER-tracking dye, and analyzed using a LSRII™ flow cytometer (BD Biosciences).

To measure protein production in the fused cells, and the parental CHO population, the cells were transfected to express secreted alkaline phosphatase (SEAP). The transfection was performed as follows:
1. Centrifuge $10^6$ cells.
2. Discard supernatant
3. Resuspend in 100 μL Cell Line Nucleofector™ Solution T
4. Add 2 μg SEAP expression plasmid
5. Transfer to electroporation cuvette
6. Electroporate using Amaxa™ Nucleofector II and preset program U-023
7. Add 0.5 ml growth medium
8. Transfer cells into 6-well plate containing 1 mL. growth medium per well FIG. 7 shows the results (specific productivity of secreted alkaline phosphatase). The expression of the marker protein (SEAP) in the fused cells shows over 4-fold improvement.

Example 2. Generation of an AAV Packaging Cell Line Containing Rep-Cap and EEV Gene Cassettes Using PiggyBac and Sleeping Beauty Transposase System 2.1 Generation of Cell Line Containing Rep-Cap (fHEK-RC)

Figure 2:
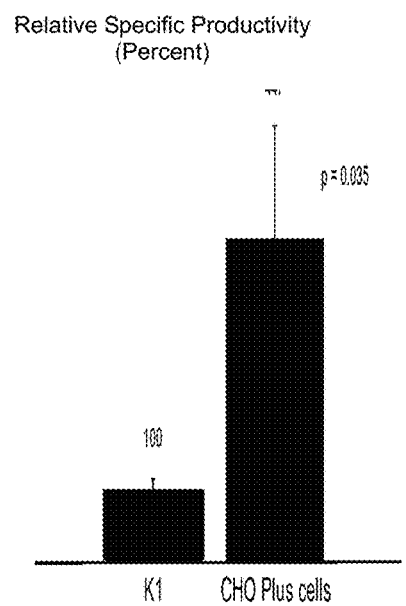
FIG. 2 shows a 4.5-fold improvement in protein production from a population of CHO cells fused and selected for high content of endoplasmic reticulum, compered with parental CHO cells. Both populations were transfected to express secreted alkaline phosphatase (SEAP).

Vector containing Rep-Cap gene cassette (FIG. 2A) is transfected into fused HEK 293F (fHEK) cells by electroporation using Bio-Rad Gene Pulser. Vector DNA and PiggyBac transposase vector are added to cell suspension, followed by electroporation using single pulse exponential decay. Post-transfection, selection medium containing selective concentration of Blasticidin is added to medium and surviving cells containing stable integration of Rep-Cap are transfected to EEV cassettes using Sleeping Beauty transposase system (FIG. 2B).

Figures 3A, 3B:
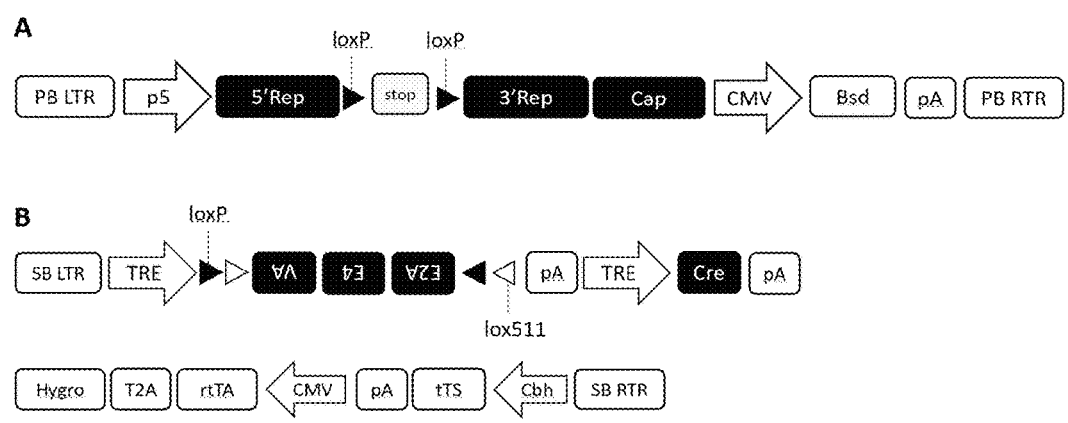
FIG. 3A is a gene map of a Rep-Cap inducible integration gene cassette for activation of E2A, E4 and VA RNA, abbreviated by EEV and Cre recombinase.
FIG. 3B maps an inducible cassette for activation of E2A, E4 and VA RNA, abbreviated by EEV and Cre recombinase.

FIG. 3A: Rep-Cap inducible integration gene cassette. Rep-Cap gene cassettes are flanked by PiggyBac transposon left and right inverted terminal repeats (LTR and RTRs respectively) containing: 1) coding region of Rep and Cap expressed by the viral endogenous promoter, p5 followed by SV40 poly A tail. Rep gene cassette is split into 5' and 3' region. A stop cassette containing transcription termination sequences flanked by two loxP sites is placed in between the 5' and 3' Rep gene cassette, in the coding region of Rep78. CMV promoter is used to drive expression of Blasticidin resistance gene, followed by poly A tail.

FIG. 3B: Inducible cassette for activation of E2A, E4 and VA RNA, abbreviated by EEV and Cre recombinase. Inducible cassette is flanked by Sleeping Beauty transposon inverted terminal repeats, left and right (abbreviated as LTRs and RTRs, respectively). EEV is in the reverse orientation, flanked by heterologous LoxP sites. Upon activation of Doxycycline, cis-recombination would result in EEV in the correct forward orientation, resulting in their expression in a dose-dependent manner. Cre recombinase is under the control of Doxycycline via TRE promoter (see below). Dox binds to reverse tetracycline-controlled transactivator (rtTA) forming Dox-rtTA complex. Dox-rtTA complex binds to Tetracycline-response element (TRE) to activate downstream target genes. The inhibitor, reverse tetracycline-controlled trans-silencer (rtTS) serve two functions: (1) minimizes the leaky expression of TRE promoter; and (2) enhances rtTA activity in the presence of Doxycyline serving as co-activator. Other abbreviations: Cbh, a CMV and chicken beta-actin hybrid promoter; Hygro, Hygromycin resistance gene; pA, SV40 poly A tail.

2.2 Generation of Cell Line Containing Rep-Cap and EEV (fHEK-AAV)

Vector containing E2A, E4 and VA gene/RNA cassette (see FIG. 2B) and Sleeping Beauty Transposase (SBT) is sequentially transfected into fHEK-RC by electroporation using Bio-Rad Gene Pulser using single pulse exponential decay. Post-transfected cells are grown in selection medium containing Blasticidin and Hygromycin and surviving cells contain stable integration of Rep-Cap and EEV cassettes.

Example 3. Generation of AAV Packaging Cell Line Containing Rep-Cap and EEV Cassettes (fHEK-SAAV)

Vector containing EEV and STAC cassettes (FIG. 3) is transfected into fHEK-RC by electroporation using Bio-Rad Gene Pulser using single pulse exponential decay. Post-transfected cells are grown in selection medium containing Blasticidin and Hygromycin and surviving cells are stably integrated with Rep-Cap, EEV, and STAC gene cassettes.

Figure 3C:
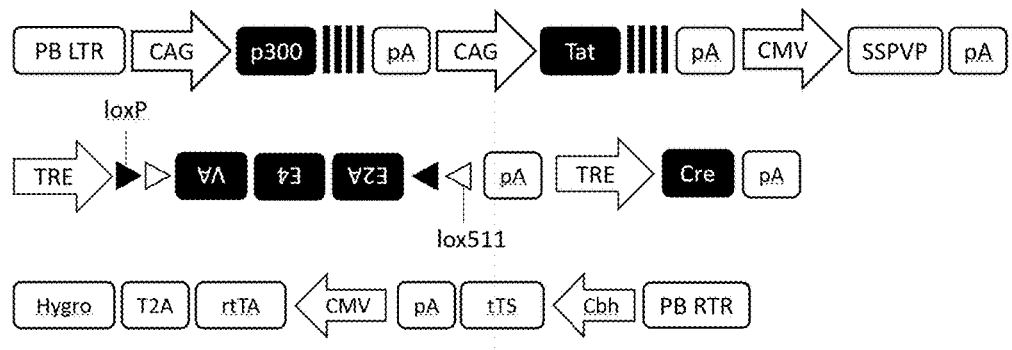
FIG. 3C maps an inducible STAC cassette for amplified synergistic activation of E2A, E4, and VA RNA (EEV).

FIG. 3C: Inducible STAC cassette for amplified synergistic activation of E2A, E4, and VA RNA (EEV). Inducible cassette is flanked by PiggyBac transposon inverted terminal repeats, left and right (abbreviated as LTRs and RTRs, respectively). Transcriptional coactivator and histone acetyl transferase (HAT), p300 and the HIV-1 Tat transcriptional activator are both tethered to multiple GCN4 peptides (denoted by black rectangles). Both fusion proteins are expressed under the control of a CMV promoter. Hybrid scaffold, SSPVP consisting of scFv fragment that binds to GCN4 peptide and transactivation domains of p53, VP64 and p65 to recruit additional transcription factors, HATs and co-activators to the basal transcription apparatus at the promoter.

Inducible cassette for activation of E2A, E4 and VA RNA, abbreviated by EEV and Cre recombinase. EEV is in the reverse orientation, flanked by heterologous LoxP sites. Upon activation of Doxycycline, cis-recombination would result in EEV in the correct forward orientation, resulting in their expression in a dose-dependent manner. Cre recombinase is under the control of TRE promoter (see below). Dox binds to reverse tetracycline-controlled transactivator (rtTA) forming Dox-rtTA complex. Dox-rtTA complex binds to Tetracycline-response element (TRE) to activate downstream target genes that would be only in the correct orientation upon Cre recombination events (e.g. EEV). The inhibitor, reverse tetracycline-controlled trans-silencer (rtTS) serve two functions: (1) minimizes the leaky expression of TRE promoter; and (2) enhances rtTA activity in the presence of Doxycyline serving as co-activator. Other abbreviations: Cbh, a CMV and chicken beta-actin hybrid promoter; Hygro, Hygromycin resistance gene; pA, SV40 poly A tail.

Example 4. Generation of Lentivirus Packaging Cell Line (fHEK-LV)

Vector containing Gag, Pol, Tat and Rev (GPTR) gene cassettes and Bsd selection marker (see FIG. 4A) is transfected into fused HEK 293F (fHEK) cells by electroporation using Bio-Rad Gene Pulser. Vector DNA and PiggyBac transposase vector are added to cell suspension, followed by electroporation using single pulse exponential decay. Cells are grown in medium containing selective concentration of Blasticidin and surviving cells are expanded, herein called fHEK-GPTR and prepared for transfection of VSV-G inducible gene cassette.

Figures 4A, 4B:
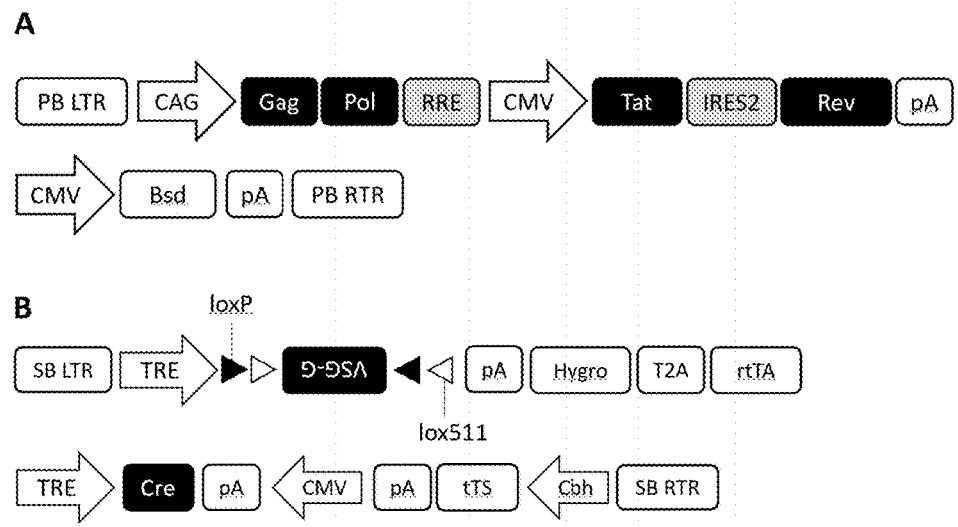
FIG. 4A is a gene map of a Gag, Pol, Tat and Rev (GPTR) integration gene cassette.
FIG. 4B maps an inducible cassette for activation of envelope VSV-G gene and gene encoding for Cre recombinase.

FIG. 4A: Gag, Pol, Tat and Rev (GPTR) integration gene cassette. GPTR gene cassettes are flanked by PiggyBac transposon left and right inverted terminal repeats (LTR and RTRs respectively). CAG is a hybrid promoter consisting of CMV early enhancer element, promoter of chicken beta-actin, and splice acceptor of the rabbit beta-globin gene. pA, SV40 poly A tail; Bsd, Blasticidin resistance gene.

Vector containing VSV-G inducible gene cassette (FIG. 4B) is transfected into fHEK-GPTR by electroporation using Bio-Rad Gene Pulser using single pulse exponential decay. Post-transfected cells are grown in selection medium containing Blasticidin and Hygromycin.

FIG. 4B: Inducible cassette for activation of envelope VSV-G gene and gene encoding for Cre recombinase. Inducible cassette is flanked by Sleeping Beauty transposon inverted terminal repeats, left and right (abbreviated as LTRs and RTRs, respectively). VSV-G is in the reverse orientation, flanked by heterologous Lox (LoxP and Lox511) sites. Cre recombinase is under the control of TRE promoter (see below). Upon activation of Doxycycline, Cre is expressed and cis-recombination would result in VSV-G in the correct forward orientation, activating VSV-G in a dose-dependent manner. Dox binds to reverse tetracycline-controlled transactivator (rtTA) forming Dox-rtTA complex. Dox-rtTA complex binds to Tetracycline-response element (TRE) to activate downstream target genes. The inhibitor, reverse tetracycline-controlled trans-silencer (rtTS) serve two functions: (1) minimizes the leaky expression of TRE promoter; and (2) enhances rtTA activity in the presence of Doxycyline serving as co-activator. Other abbreviations: Cbh, a CMV and chicken beta-actin hybrid promoter; Hygro, Hygromycin resistance gene; pA, SV40 poly A tail.

Example 5. Generation of Lentivirus Packaging Cell Line Containing GPTR, Inducible Envelope, and STAC Gene Cassettes (fHEK-SLV)

Vector containing VSV-G and STAC cassettes (FIG. 5) is transfected into fHEK-GPTR by electroporation using Bio-Rad Gene Pulser using single pulse exponential decay. Post-transfected cells are grown in selection medium containing Blasticidin and Hygromycin.

FIG. 5: Inducible STAC cassette for amplified synergistic activation of VSV-G gene as well as packaging genes, Gag, Pol, Tat and Rev (GPTR, see FIG. 4). Inducible cassette is flanked by PiggyBac transposon inverted terminal repeats, left and right (abbreviated as LTRs and RTRs, respectively). Transcriptional coactivator and histone acetyl transferase (HAT), p300 and the HIV-1 Tat transcriptional activator are both tethered to multiple GCN4 peptides (denoted by black rectangles). Both fusion proteins are expressed under the control of a CMV promoter. Hybrid scaffold, SSPVP consisting of scFv fragment that binds to GCN4 peptide and transactivation domains of p53, VP64 and p65 to recruit additional transcription factors, HATs and co-activators to the basal transcription apparatus at the promoter.

Inducible cassette for activation of envelope VSV-G gene and gene encoding for Cre recombinase. VSV-G is in the reverse orientation, flanked by heterologous Lox (LoxP and Lox511) sites. Upon activation of Doxycycline, Cre is expressed and cis-recombination would result in VSV-G in the correct forward orientation, activating VSV-G gene expression in a dose-dependent manner. Upon Doxyline induction, Dox binds to reverse tetracycline-controlled transactivator (rtTA). Dox-rtTA complex binds to Tetracycline-response element (TRE) to activate downstream target genes. The inhibitor, reverse tetracycline-controlled trans-silencer (rtTS) serve two functions: (1) minimizes the leaky expression of TRE promoter; and (2) enhances rtTA activity in the presence of Doxycyline serving as co-activator. Other abbreviations: Cbh, a CMV and chicken beta-actin hybrid promoter; Hygro, Hygromycin resistance gene; pA, SV40 poly A tail.

5.1 Oher Possible Gene Modifications and Potential Benefits

Chromatin modifications can contribute both positively and negatively to gene transcription. Actively transcribed genes are enriched in acetylation of histones in both the promoter and the 5' regions of coding region of genes. Of the known enzymes histone acetyltransferases (HATs) to-date, CBP/p300 globally acetylates thousands of sites, many of which are signature histones sites for active gene transcription regions (Weinert et al., 2018). p300/CBP is often referred as a single entity due to their extensive homology and functional similarities (reviewed in Kouzarides 2007). p300/CBP also serve as a transcriptional coactivator, proteins which bridges transcription activators and the components of the basal transcriptional apparatus (reviewed in Janknecht and Hunter, 1996). P300 acts as a transcriptional coactivator for large repertoires of signaling pathways that include HIV-1 viral machinery and E1A recruitment for adenoviruses.

Benefits of enhanced viral production can be attained through increased exogenous expression of a global HAT such as p300/CBP or attenuation of HDAC, an active competitor for p300. HDAC deacetylates the same site as p300/CBP (Li et al., 2014).

Example 6. Generation of Packaging Cell Line with Exogenous Expression of p300

Vector containing coding region of p300 expressed under the control of a CMV promoter and Blasticidin resistance gene (FIG. 6A) is transfected into fused HEK 293F (fHEK) cells by electroporation using Bio-Rad Gene Pulser using single pulse exponential decay. Selection medium containing Blasticidin is added to medium and surviving cells containing stable integration of p300 are expanded.

FIG. 6A is a diagram of a p300 integration gene cassette. p300 gene is flanked by CMV promoter and SV40 poly A tail. Blasticidin (Bsd) resistance gene cassette is placed downstream of p300 gene cassette containing CMV promoter, gene encoding for Bsd, and SV40 poly A tail. FIG. 6B shows a HDAC shRNA gene cassette. HDAC shRNA is flanked by U6 promoter for shRNA expression. Blasticidin (Bsd) resistance gene cassette is placed downstream of shRNA expression cassette containing CMV promoter, gene encoding for Bsd, and SV40 poly A tail. FIG. 6C shows a Spliced Xbp1 (Xbp1s) gene cassette. Xbp1s gene is flanked by CMV promoter and SV40 poly A tail. Blasticidin (Bsd) resistance gene cassette is placed downstream of Xbp1s gene cassette containing CMV promoter, gene encoding for Bsd, and SV40 poly A tail.

Example 7. Generation of Packaging Cell Line with Knockdown of HDAC

Packaging of lentivirus is performed by complexing U6-HDAC shRNA transfer vector (FIG. 6B) with helper, packaging and envelope vectors using polyethylenimine. Complex is added to HEK 293 cells. Supernatant is harvested post-transfection and lentivirus titer is assayed by sandwich ELISA. fHEK are infected with lentivirus particles containing U6-HDAC shRNA. Transduced cells are grown in selection medium containing Blasticidin and surviving cells containing stable integration of U6-HDAC shRNA are expanded.

Further enhancement of endoplasmic reticulum (ER) can be achieved through activation of the Unfolded Protein Response (UPR) pathways. Under ER stress, unspliced Xbp1 mRNA is cleaved by activated stress sensor Ire1α, generated spliced Xbp1 (Xbp1s). Translated Xbp1s is translocated to the nucleus hundreds of target genes encoding for ER molecular chaperones, folding enzymes, and ER-associated protein degradation (ERAD) Enhanced Xbp1s can increase ER biogenesis in mammary epithelial cells (Sharmin et al., 2021). Benefits for enhanced ER function by means of increasing expression of spliced Xbp1 can be leveraged for elevated virus production.

Example 8. Generation of Packaging Cell Line with Exogenous Expression of Spliced Xbp1s Vector containing coding region of Xbp1 spliced (Xbp1s) expressed under the control of a CMV promoter and Blasticidin resistance gene (see FIG. 6C) is transfected into fused HEK 293F (fHEK) cells by electroporation using Bio-Rad Gene Pulser using single pulse exponential decay. Selection medium containing Blasticidin is added to medium and surviving cells contain stable integration of Xbp1s.

Example 9: Protocol for Selection of Fused Cells with High Mitochondria and High ROS To screen for different phenotypes of mitochondria and reactive oxygen species (ROS), hybrids were stained with CellROX® Deep Red Reagent, a fluorogenic probe for measuring cellular oxidative stress in cells; TMRM (tetramethyl rhodamine methyl ester), which measures the membrane potential of mitochondria in living cells; and Biotracker 405 Blue Mitochondria, which stains the mitochondria membrane. LIVE/DEAD Fixable NIR was used in this experiment to stain for live cells.

FIG. 8 shows the workflow used. Fused cells were cultured in complete, animal origin free (AOF), chemically defined cell culture medium: CDM4 PerMAb+6 mM L-Glutamine and detached using StemPro™ Accutase™ Cell Dissociation Reagent. Samples of cells were combined with a calculated volume of each dye to final concentrations in ~200 mL of cell suspension containing $1 \times 10^8$ cells in a 500 mL shake flask. Samples were incubated @120 rpm in shaker overnight at 37° C. with 8% $CO_2$.

For cell sorting, 200 mL of cell sample was centrifuged at 300×g for 5 min. The cell pellet was suspended in Accutase cell dissociation reagent, diluted, and strained into a sterile 50 mL centrifuge tubes. Cells were sorted using a Sony SH800S Cell Sorter with the following gates: Gate 1—cell ID gate; Gate 2—singlets gate; Gate 3—live cells gate; Gate 4—Biotracker 405 Blue Mitochondria (select the top 10%); Gate 5—TMRE×CellROX Deep Red (select the top 10% quadrant).

Populations of 500,000 sorted cells were expanded for 4-5 days and used for single-cell cloning in 96-well plates containing 150 µl of medium per well. Once individual wells were 80% confluent, they were expanded stepwise to 125 mL shake flasks, and used to create cell banks.

Example 10. Protocol for Transient Transfection of HEK 291 Cells to Express AAV Capsids Containing a Reporter Gene Useful sources for reagents are the AAV-MAX system, available from ThermoFisher, the VirusGEN® AAV Transfection Kit, and the AAVpro helper free systems for various serotypes of AAV from Takara.

The day prior to transfection, host cells were seeded 125-mL cell culture flask at a density of $3\times10^6$ viable cells/mL in 25 mL of complete, animal origin free (AOF), chemically defined cell culture medium (CDM4 PerMAb) with 6 mM L-glutamine, and grown to a density of $3.0\times10^6$ viable cells per mL with >90% viability. Cells were centrifuged at 300×g in conical tubes and resuspended in 25 mL of Viral Production Medium. After transfer to a new shake flask, 250 μL of AAV-MAX Enhancer was added. Cells were cultured in a 37° C. incubator on an orbital shaker until the DNA/transfection complexation was complete.

FIG. 8 maps the plasmids used to make AAV vectors containing an enhanced green fluorescent protein (EGFP) reporter gene for purposes of screening cell hybrids for virus production. A mix of these plasmids was prepared as shown in TABLE 4.

TABLE 4

AAV plasmids used for transfection

| Plasmid function | Size (bp) | Name | Molar Ratio | Size × ratio | μg DNA | DNA conc (μg/μl) |
|---|---|---|---|---|---|---|
| Payload | 5118 | pAAV-EGFP | 3 | 15,354 | 13.1 | 1.0 |
| Rep/Cap - pRC1 | 7330 | pRC1 | 2 | 14,660 | 12.5 | 1.0 |
| Helper | 11635 | pHelper | 5 | 58,175 | 49.5 | 1.0 |

75 μL of Trans-IT VirusGEN® was added to the plasmids in AAV CFS&E solution, and incubated at room temperature for 15 minutes to allow transfection complexes to form. 2.7 of this mixture was added to each 125 mL flask, and placed back in the incubator for 12 to 18 h. 0.3 mL of 0.5 M sodium butyrate was added, and the cells were harvested 72 h after transfection.

PUBLICATIONS

Chan K Y, Jang M J, Yoo B B, Greenbaum A, Ravi N, Wu W L, Sanchez-Guardado L, Lois C, Mazmanian S K, Deverman B E, Gradinaru V. Engineered AAVs for efficient noninvasive gene delivery to the central and peripheral nervous systems. Nat Neurosci. 2017 August; 20(8): 1172-1179. doi: 10.1038/nn.4593. Epub 2017 Jun. 26. PMID: 28671695; PMCID: PMC5529245.

Colberg-Poley A M, Patel M B, Erezo D P, Slater J E. Human cytomegalovirus UL37 immediate-early regulatory proteins traffic through the secretory apparatus and to mitochondria. J Gen Virol. 2000 July; 81(Pt 7):1779-89. doi: 10.1099/0022-1317-81-7-1779. PMID: 10859384.

Cook K C, Moreno J A, Jean Beltran P M, Cristea I M. Peroxisome Plasticity at the Virus-Host Interface. Trends Microbiol. 2019; 27(11):906-914. doi:10.1016/j.tim.2019.06.006

Das A T, Tenenbaum L, Berkhout B. Tet-On Systems For Doxycycline-inducible Gene Expression. Curr Gene Ther. 2016; 16(3):156-67.

Gray S J, Foti S B, Schwartz J W, et al. Optimizing promoters for recombinant adeno-associated virus-mediated gene expression in the peripheral and central nervous system using self-complementary vectors. Hum Gene Ther. 2011; 22(9):1143-1153. doi:10.1089/hum.2010.245

James J A, Aggarwal A K, Linden R M, Escalante C R. Structure of adeno-associated virus type 2 Rep40-ADP complex: insight into nucleotide recognition and catalysis by superfamily 3 helicases. Proc Natl Acad Sci USA. 2004; 101(34):12455-12460. doi:10.1073/pnas.0403454101

James J A, Escalante C R, Yoon-Robarts M, Edwards T A, Linden R M, Aggarwal A K. Crystal structure of the SF3 helicase from adeno-associated virus type 2. Structure. 2003 August; 11(8):1025-35. doi: 10.1016/s0969-2126(03)00152-7. PMID: 12906833.

Janknecht R, Hunter T. Transcription. A growing coactivator network. Nature. 1996 Sep. 5; 383(6595):22-3. doi: 10.1038/383022a0. PMID: 8779707.

Kouzarides T. Chromatin modifications and their function. Cell. 2007 Feb. 23; 128(4):693-705. doi: 10.1016/j.cell.2007.02.005. PMID: 17320507.

Li X, Yang H, Huang S, Qiu Y. Histone deacetylase 1 and p300 can directly associate with chromatin and compete for binding in a mutually exclusive manner. PLoS One. 2014 Apr. 10; 9(4):e94523. doi: 10.1371/journal.pone.0094523. PMID: 24722339; PMCID: PMC3983199.

Linden R M, Berns K I. Molecular biology of adeno-associated viruses. Contrib Microbiol. 2000; 4:68-84. doi: 10.1159/000060327. PMID: 10941571.

Lochmann T L, Bann D V, Ryan E P, Beyer A R, Mao A, Cochrane A, Parent U. N C-mediated nucleolar localization of retroviral gag proteins. Virus Res. 2013 February; 171(2):304-18. doi: 10.1016/j.virusres.2012.09.011. Epub 2012 Oct. 2. PMID: 23036987; PMCID: PMC3578147.

Matsushita T, Okada T, Inaba T, Mizukami H, Ozawa K, Colosi P. The adenovirus E1A and E1B19K genes provides a helper function for transfection-based adeno-associated virus vector production. J Gen Virol. 2004, 85: 2209-2214. DOI 10.1099/vir.0.79940-0

Mavinakere M S, Colberg-Poley A M. Internal cleavage of the human cytomegalovirus UL37 immediate-early glycoprotein and divergent trafficking of its proteolytic fragments. J Gen Virol. 2004 July; 85(Pt 7):1989-1994. doi: 10.1099/vir.0.80094-0. PMID: 15218184.

Mougiakos I, Beisel C L. CRISPR transposons on the move. Cell Host Microbe. 2021 May 12; 29(5):675-677. doi: 10.1016/j.chom.2021.04.012. PMID: 33984272.

Qiao C, Wang B, Zhu X, Li J, Xiao X. A novel gene expression control system and its use in stable, high-titer 293 cell-based adeno-associated virus packaging cell lines. J Virol. 2002 December; 76(24):13015-27. doi: 10.1128/jvi.76.24.13015-13027.2002. PMID: 12438627; PMCID: PMC136669.

Qiao, Chunping et al. "Feasibility of generating adeno-associated virus packaging cell lines containing inducible adenovirus helper genes." Journal of virology vol. 76.4 (2002): 1904-13. doi:10.1128/jvi.76.4.1904-1913.2002

Ravindran M S, Bagchi P, Cunningham C N, Tsai B. Opportunistic intruders: how viruses orchestrate E R functions to infect cells. Nat Rev Microbiol. 2016; 14(7): 407-420. doi:10.1038/nrmicro.2016.60

Sanber, K., Knight, S., Stephen, S. et al. Construction of stable lentiviral vector packaging cell lines for clinical lentiviral vector production. Sci Rep 5, 9021 (2015). https://doi.org/10.1038/srep09021

Sharmin M M, Hayashi S, Miyaji M, Ishizaki H, Matsuyama H, Haga S, Yonekura S. Insulin-like growth factor-1 induces IRE1-XBP1-dependent endoplasmic reticulum biogenesis in bovine mammary epithelial cells. J Dairy Sci. 2021 November; 104(11):12094-12104. doi: 10.3168/jds.2021-20268. Epub 2021 Aug. 5. PMID: 34364639.

Smith J J, Aitchison J D. Peroxisomes take shape. Nat Rev Mol Cell Biol. 2013; 14(12):803-817. doi:10.1038/nrm3700

Strang B L, Boulant S, Kirchhausen T, Coen D M. Host cell nucleolin is required to maintain the architecture of human cytomegalovirus replication compartments. mBio. 2012 Feb. 7; 3(1):e00301-11. doi: 10.1128/mBio.00301-11. PMID: 22318319; PMCID: PMC3280463.

Tal Kafri, Henriette van Praag, Ling Ouyang, Fred H. Gage, Inder M. Verma Journal of Virology January 1999, 73 (1) 576-584; DOI: 10.1128/JVI.73.1.576-584.1999

Tanenbaum M E, Gilbert L A, Qi L S, Weissman J S, Vale R D. A protein-tagging system for signal amplification in gene expression and fluorescence imaging. Cell. 2014 Oct. 23; 159(3):635-46. doi: 10.1016/j.cell.2014.09.039. Epub 2014 Oct. 9. PMID: 25307933; PMCID: PMC4252608.

Williamson C D, DeBiasi R L, Colberg-Poley A M. Viral product trafficking to mitochondria, mechanisms and roles in pathogenesis. Infect Disord Drug Targets. 2012 February; 12(1):18-37. doi: 10.2174/187152612798994948. PMID: 22034933; PMCID: PMC4435936.

Wistuba A, Kern A, Weger S, Grimm D, Kleinschmidt J A. Subcellular compartmentalization of adeno-associated virus type 2 assembly. J Virol. 1997 February; 71(2): 1341-52. doi: 10.1128/JVI.71.2.1341-1352.1997. PMID: 8995658; PMCID: PMC191189.

Yuan, Z., Qiao, C., Hu, P., Li, J., & Xiao, X. (2011). A versatile adeno-associated virus vector producer cell line method for scalable vector production of different serotypes. Human gene therapy, 22(5), 613-624. https://doi.org/10.1089/hum.2010.241

European patent E P 2316955 B 1: Engineered cell lines engineered with higher expression of Xbp1 and Atf6 by means of transfecting a vector containing the coding region of Xbp1 or Atf6 or plurality of Xbp1 and Atf6 under the control of constitutive promoter(s).

U.S. Pat. No. 6,989,264: Methods for generating high titer helper-free preparations of released recombinant AAV vectors.

U.S. Pat. No. 7,745,592: Cumate-inducible expression system for eukaryotic cells U.S. Pat. No. 8,728,759: Reverse cumate repressor mutant U.S. Pat. No. 8,828,719. Engineered cell lines transfected with Ero1 and Xbp1 under the control of a constitutive promoter.

U.S. Pat. No. 9,441,245: Lentiviral packaging cell line containing HIV-1 gag, pol and tat genes integrated into its genome using baculo-AAV hybrid system.

U.S. Pat. No. 10,329,594: Cell lines for high level production of protein-based pharmaceuticals U.S. Pat. No. 11,441,132: Mutated sleeping beauty transposase U.S. Pat. No. 11,649,449: Hybrid cell lines for high level production of a target protein

INCORPORATION BY REFERENCE

For all purposes in the United States of America, each and every publication and patent document referred to in this disclosure is incorporated herein by reference in its entirety for all purposes to the same extent as if each such publication or document was specifically and individually indicated to be incorporated herein by reference.

PRACTICE OF THE CLAIMED INVENTION

The technology provided in this disclosure and its use are described within a hypothetical understanding of general principles of virus and pharmaceutical manufacture. These discussions are provided for the edification and interest of the reader, and are not intended to limit the practice of the claimed invention. All of the products and methods claimed in this application may be used for any suitable purpose without restriction, unless otherwise indicated or required.

While this disclosure has been described with reference to the specific embodiments, changes can be made and equivalents can be substituted to adapt this disclosure to a particular context or intended use as a matter of routine experimentation, thereby achieving benefits of this disclosure without departing from the scope of what is claimed.

The invention claimed is:

1. A process for establishing a packaging cell line for high efficiency production of viral vectors or particles, the process comprising:
   (a) providing a starter population of cultured cells that are able to package a species of viral vector or particle when genetically altered to express genes that encode the viral vector or particle;
   (b) forming hybrid cells from the starter population, each comprising two or more cells;
   (c) dividing the hybrid cells into a plurality of aliquots;
   (d) taking a sample of cells from each of the aliquots;
   (e) genetically altering cells in each of the samples to express genes that encode a test viral vector or particle of said species;
   (f) measuring production of the test viral vector or particle by cells in each of the samples, thereby identifying which aliquots contain cells that produce a higher functional titer of the test viral vector or particle, compared with cells in other aliquots;
   (g) expanding in culture cells from one or more of the aliquots identified in step (f), thereby establishing a packaging cell line which when genetically altered to express said species of viral vector or particle, produces more viral vector or particle per liter of culture fluid, compared with the starter population.

2. The process of claim 1, wherein cells in each of the samples is also genetically altered in step (e) with a transgene that constitutes or encodes a payload, thereby adapting the cells to produce a viral vector or a viral particle encapsulating said payload.

3. The process of claim 2, wherein the transgene encodes a reporter protein that emits a detectable signal.

4. The process of claim 3, wherein the reporter protein is enhanced green fluorescent protein (eGFP).

5. The process of claim 2, wherein the payload is all therapeutic payload for use in medical treatment.

6. The process of claim 1, wherein the aliquots or clones used to establish the packaging cell line in step (d) are chosen at least in part because they produce more viral capsids or particles per cell compared with other aliquots or clones formed in step (b).

7. The process of claim 2, wherein the aliquots or clones used to establish the packaging cell line in step (d) are chosen at least in part because they produce a greater proportion of capsids that contain the payload compared with other aliquots or clones formed in step (b).

8. The process of claim 1, further comprising selecting hybrid cells that have a faster rate of proliferation compare with other hybrids formed in step (b).

9. The process of claim 1, comprising cloning the hybrid cells before or after any of steps (c) to (g).

10. The process of claim 1, wherein the starter population of cultured cells is a culture of CHO cells, human embryonic kidney 293 (HEK 293) cells, or HeLa cells.

11. The process of claim 1,
wherein the packaging cell line established in step (g), when genetically altered to express said species of viral vector or particle, produces more than twice as much of the viral vector or particle per liter of culture fluid, compared with the starter population.

12. The process of claim 1, further comprising sorting or separating the hybrid cells for a higher content of mitochondria and/or a higher content of reactive oxygen species per cell, compared with other hybrid cells formed in step (b).

13. The process of claim 12, wherein the sorting or separating is done with a fluorescent activated cell sorter (FACS) using a functional or vital dye that stains cells for the amount of mitochondria or the concentration of reactive oxygen species.

14. The process of claim 12, wherein the sorting or separating is done by testing hybrid cells in a sample from each of the aliquots or clones for the presence or absence of said cell phenotype.

15. The process of claim 1, further comprising genetically altering the hybrid cells before or after establishing the packaging cell line such that the cells express one or more transgenes encoding a viral vector or particle of said species and a transgene that encodes a therapeutic payload, thereby adapting the cells to produce a viral vector or particle containing said therapeutic payload.

16. The process of claim 15, wherein the therapeutic payload includes a nucleic acid configured for expression in a human subject administered with the viral vector or particle.

17. The process of claim 15, wherein the therapeutic payload includes a protein configured for delivery into cells of a human subject administered with the viral vector or particle.

18. The process of claim 15, wherein the therapeutic payload is configured for gene therapy of the subject.

19. The process of claim 15, wherein the therapeutic payload is configured for inducing or promoting a specific immunological response in the subject.

20. The process of claim 15, wherein the therapeutic payload is an antigen of SARS-COV-2, the virus that causes COVID-19, or a nucleic acid encoding said antigen.

* * * * *